(12) United States Patent
Dudhedia et al.

(10) Patent No.: US 12,042,210 B2
(45) Date of Patent: Jul. 23, 2024

(54) TISSUE/VESSEL SEALER AND CUTTER WITH VARIABLE SHAPES OF JAW ASSEMBLY WITH PARTIAL DLC COATING

(71) Applicants: K-NINE WRITING SYSTEMS PVT. LTD., Mumbai (IN); Uddhavraj Dudhedia, Mumbai (IN)

(72) Inventors: Uddhavraj Dudhedia, Mumbai (IN); S. Dipen Shah, Mumbai (IN); Sandeep Walde, Thane (IN)

(73) Assignee: BLUE PHOENIX TECHNOLOGIES PRIVATE LIMITED, Maharashtra (IN)

( * ) Notice: Subject to any disclaimer, the term of this patent is extended or adjusted under 35 U.S.C. 154(b) by 569 days.

(21) Appl. No.: 16/071,392

(22) PCT Filed: Jan. 23, 2017

(86) PCT No.: PCT/IN2017/000016
§ 371 (c)(1),
(2) Date: Jul. 19, 2018

(87) PCT Pub. No.: WO2017/130214
PCT Pub. Date: Aug. 3, 2017

(65) Prior Publication Data
US 2019/0029746 A1 Jan. 31, 2019

(30) Foreign Application Priority Data

Jan. 25, 2016 (IN) .............................. 201621002675

(51) Int. Cl.
*A61B 18/14* (2006.01)
*A61B 17/28* (2006.01)
(Continued)

(52) U.S. Cl.
CPC .......... *A61B 18/1445* (2013.01); *A61B 17/28* (2013.01); *A61B 17/282* (2013.01);
(Continued)

(58) Field of Classification Search
None
See application file for complete search history.

(56) References Cited

U.S. PATENT DOCUMENTS 6,312,430 B1 * 11/2001 Wilson ............... A61B 18/1445
606/174
8,887,373 B2 * 11/2014 Brandt .................... B29C 70/88
29/527.4
(Continued)

FOREIGN PATENT DOCUMENTS

WO WO-9940858 A1 8/1999

OTHER PUBLICATIONS

International Search Report issued in PCT/IN2017/000016 dated Jun. 22, 2017.

*Primary Examiner* — Ronald Hupczey, Jr.
(74) *Attorney, Agent, or Firm* — Dennemeyer & Associates LLC; Victoria Friedman

(57) ABSTRACT

A surgical instrument having vessel/tissue sealer and/or cutter jaws are described designed with variety of shapes and more safer jaws. Optional ceramic insert, partial DLC coating on the substantially back portion and TiN coating is a combination in the jaw assembly which increases its safety, performance and reusability compared to other existing jaws.

11 Claims, 47 Drawing Sheets

(51) Int. Cl.
*A61B 17/29* (2006.01)
*A61B 17/295* (2006.01)
*A61B 17/32* (2006.01)
*A61B 18/00* (2006.01)
*A61B 34/00* (2016.01)

(52) U.S. Cl.
CPC ............ *A61B 17/29* (2013.01); *A61B 17/295* (2013.01); *A61B 18/00* (2013.01); *A61B 2017/2926* (2013.01); *A61B 2017/2948* (2013.01); *A61B 2017/320073* (2017.08); *A61B 2018/00083* (2013.01); *A61B 2018/00119* (2013.01); *A61B 2018/0013* (2013.01); *A61B 2018/00601* (2013.01); *A61B 2018/0063* (2013.01); *A61B 34/70* (2016.02)

(56) References Cited

U.S. PATENT DOCUMENTS

| | | | | |
|---|---|---|---|---|
| 2002/0072746 A1* | 6/2002 | Lingenfelder | ..... | A61B 18/1442 606/51 |
| 2012/0083783 A1* | 4/2012 | Davison | ............ | A61B 18/1445 606/45 |
| 2012/0259331 A1* | 10/2012 | Garrison | ............ | A61B 18/1445 606/51 |
| 2013/0296922 A1* | 11/2013 | Allen, IV | .......... | A61B 18/1445 606/205 |
| 2015/0018826 A1 | 1/2015 | Boudreaux | | |
| 2018/0250066 A1* | 9/2018 | Ding | ................. | A61B 18/1442 |

\* cited by examiner

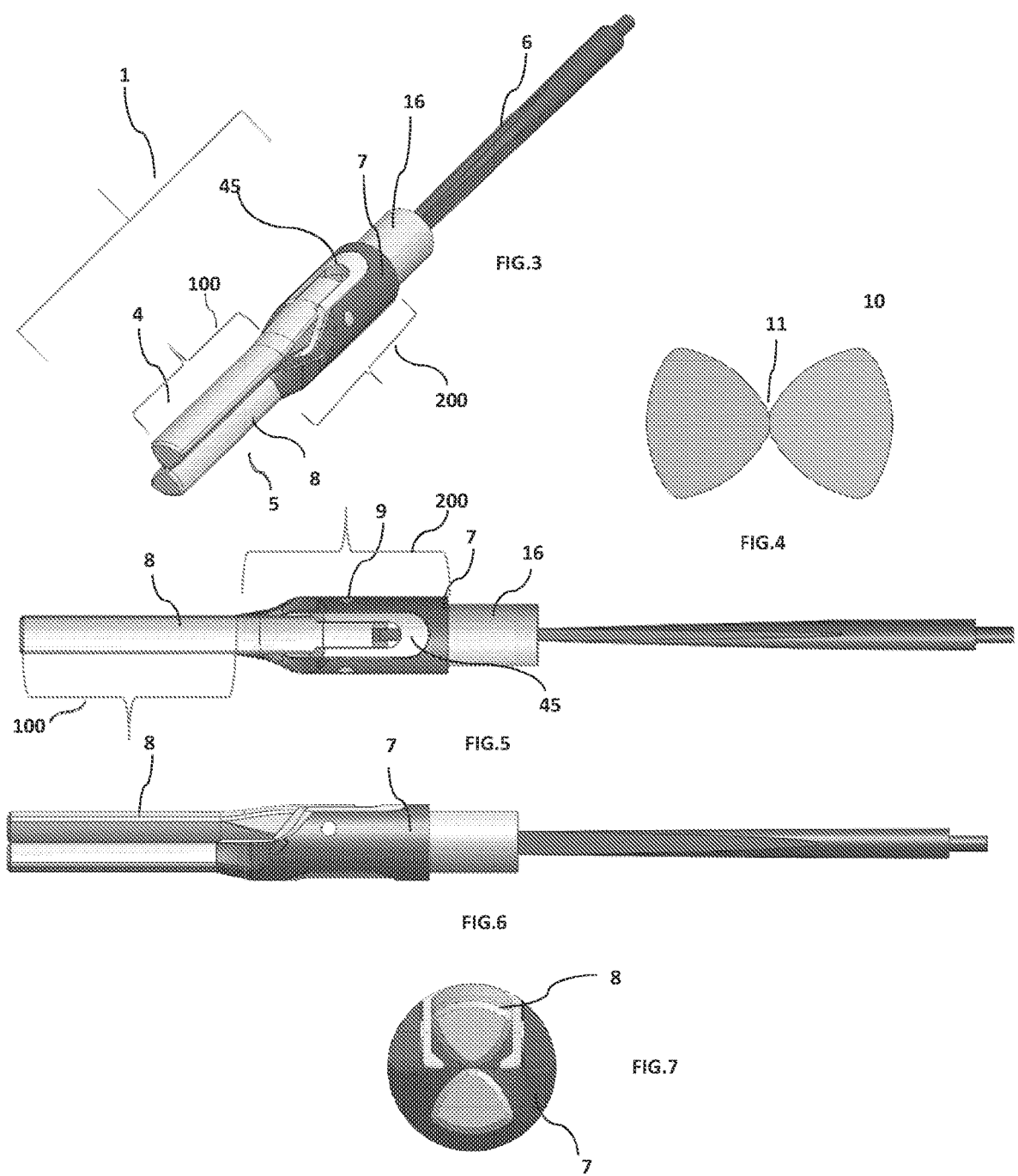

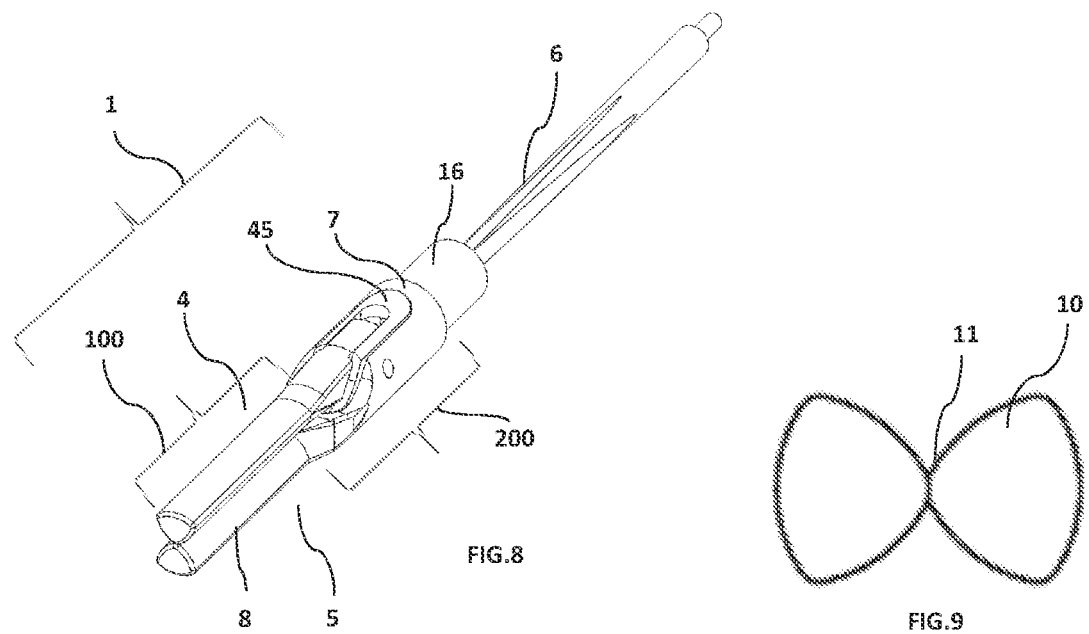
FIG.8
FIG.9
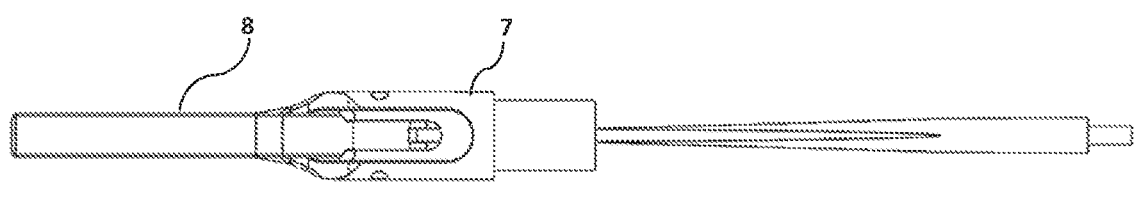
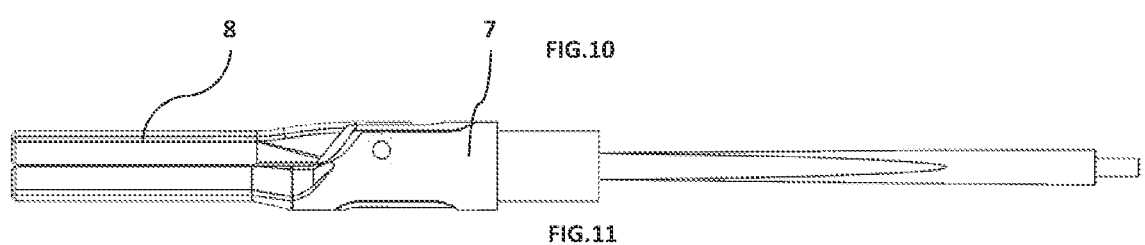
FIG.10
FIG.11
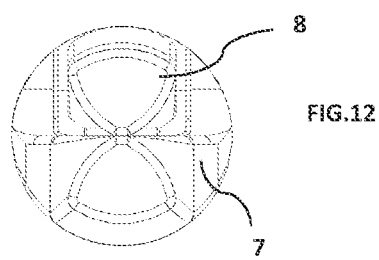
FIG.12

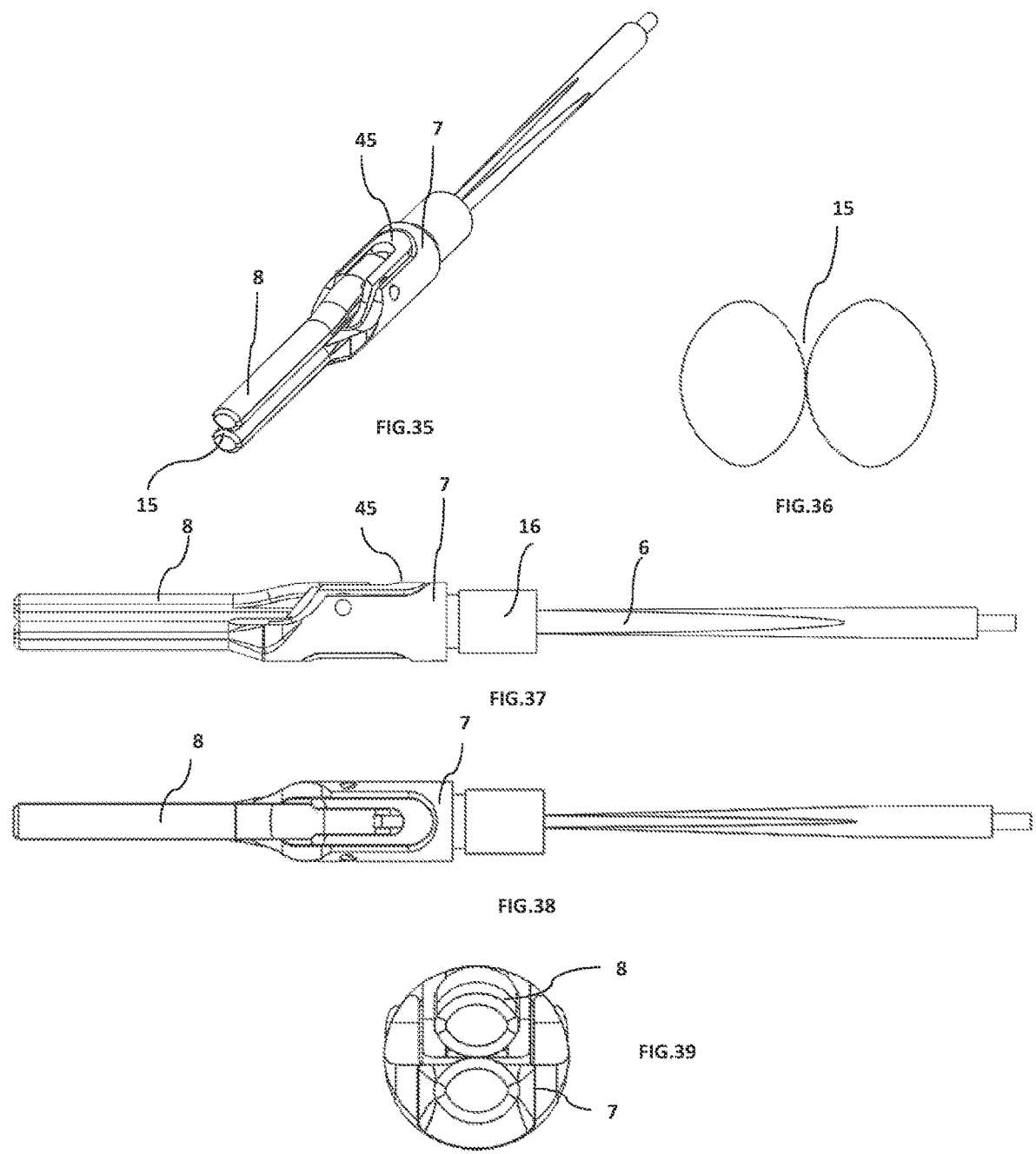

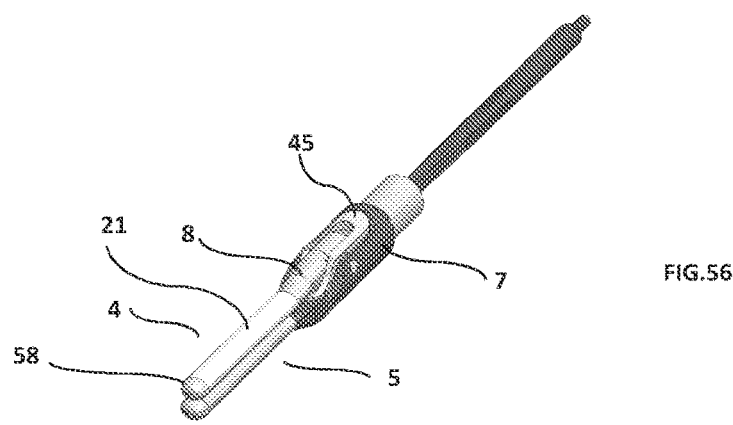
FIG.56
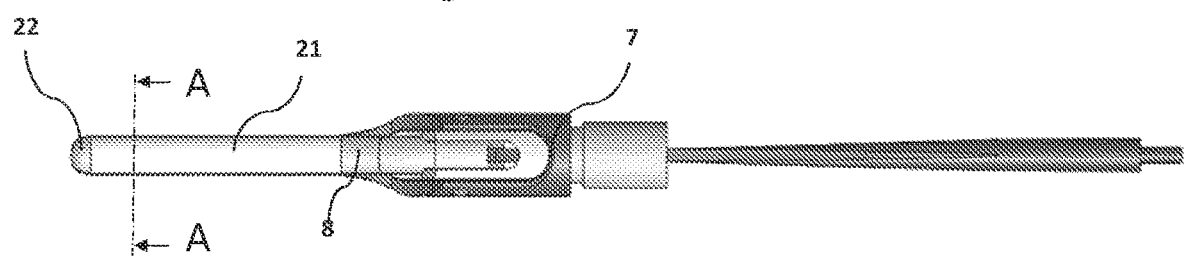
FIG.57
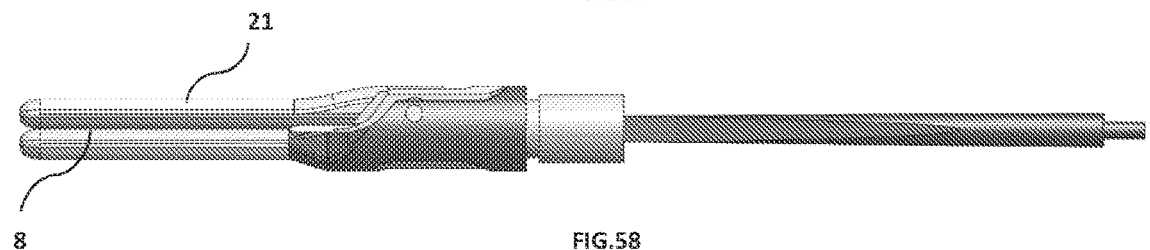
FIG.58
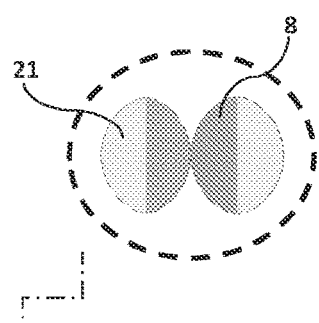
FIG.59
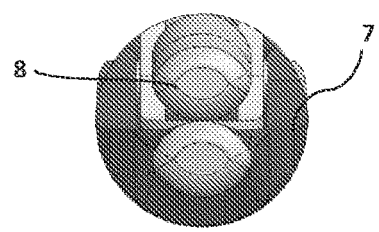
FIG.60
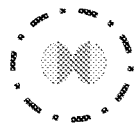
Section A-A Section A-A Detail 'X'

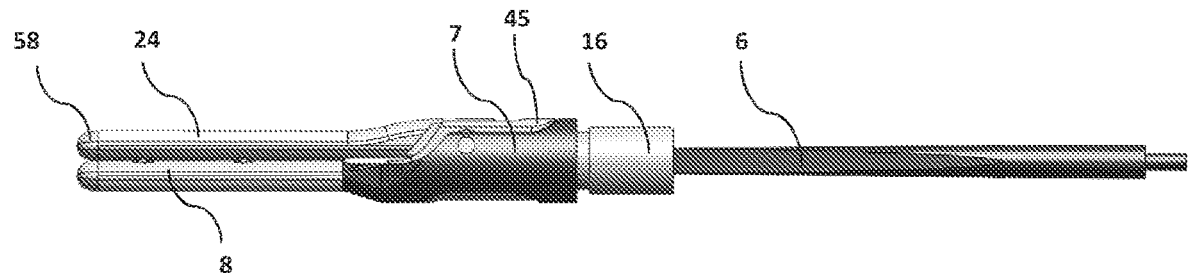
FIG.70
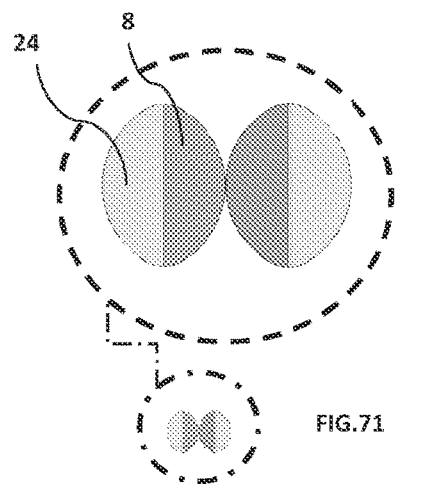
FIG.71
Section A-A
FIG.72
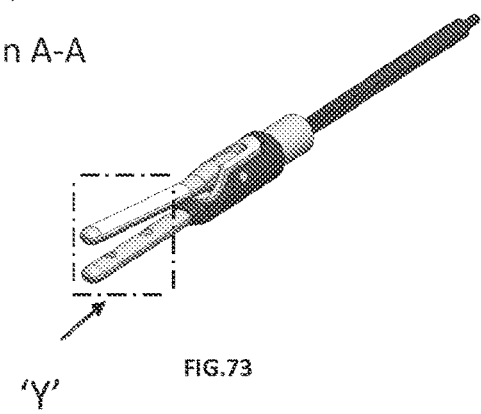
FIG.73
'Y'
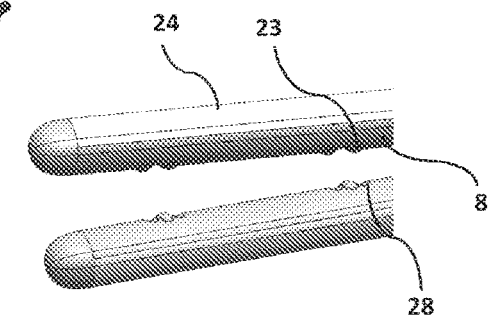
Detail 'Y'
FIG.74

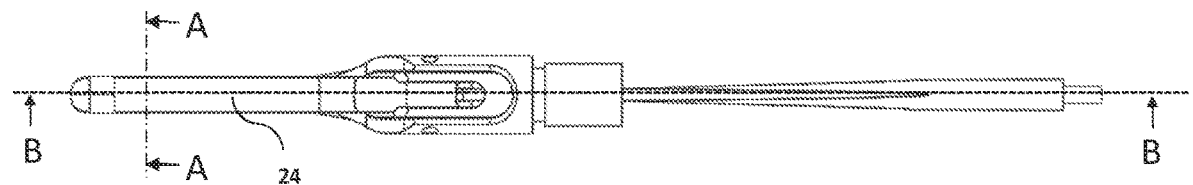
FIG.75
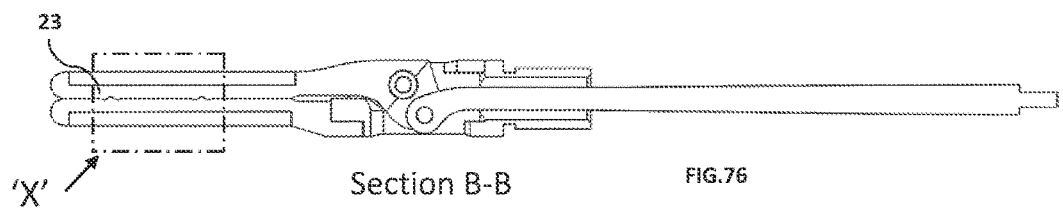
Section B-B   FIG.76
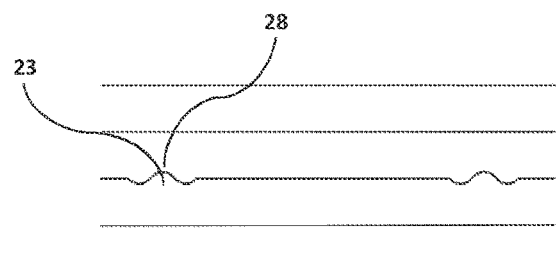
FIG.77
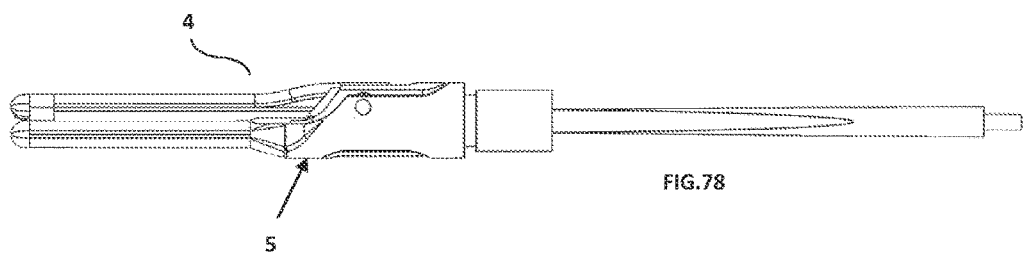
FIG.78

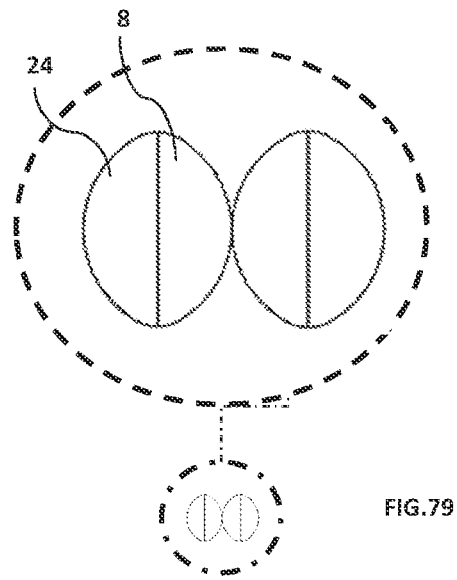
FIG.79
Section A-A
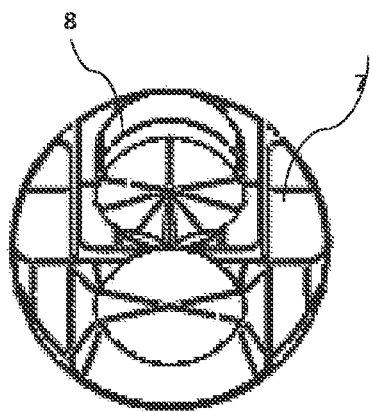
FIG.80
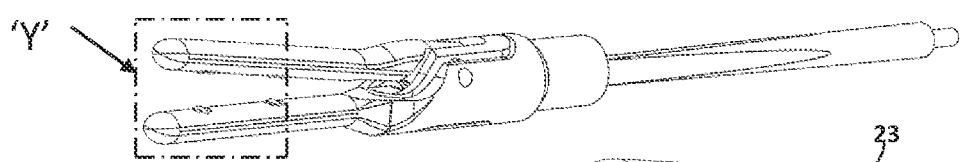
FIG.81
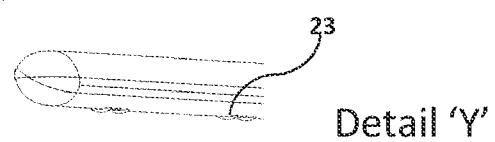
Detail 'Y'
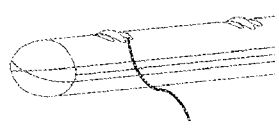
FIG.82

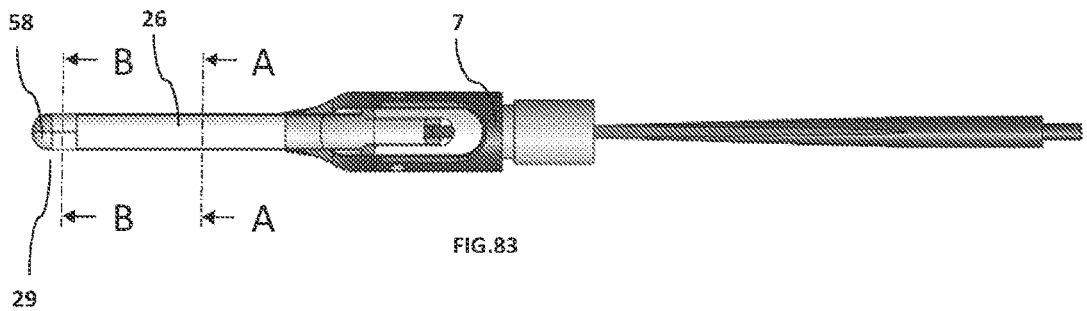
FIG.83
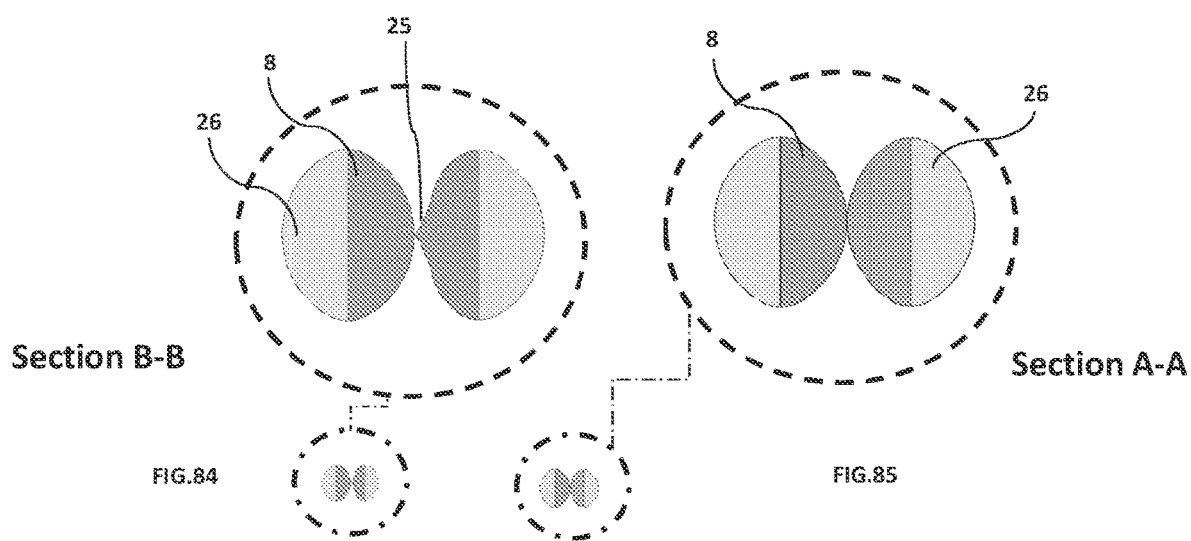
Section B-B  
FIG.84
Section A-A  
FIG.85
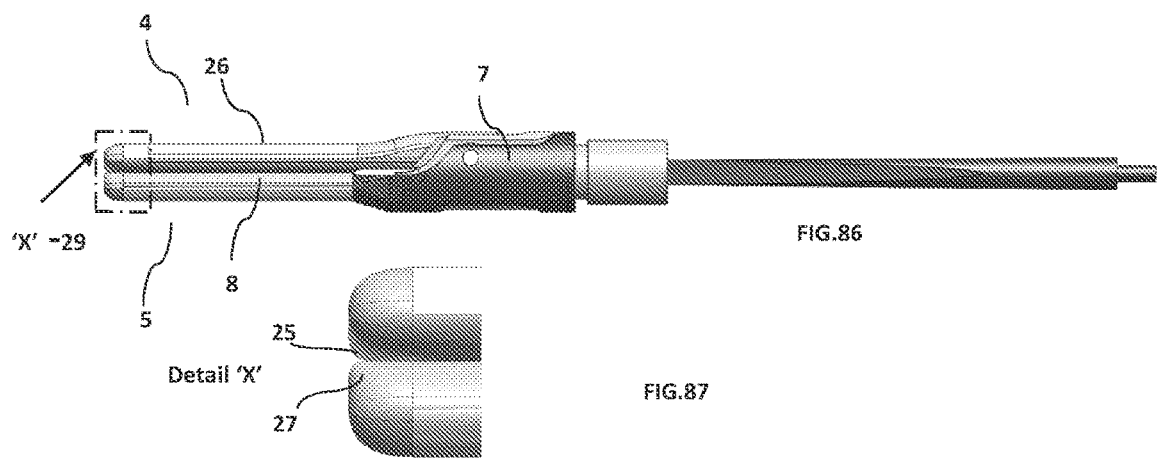
FIG.86
Detail 'X'  
FIG.87

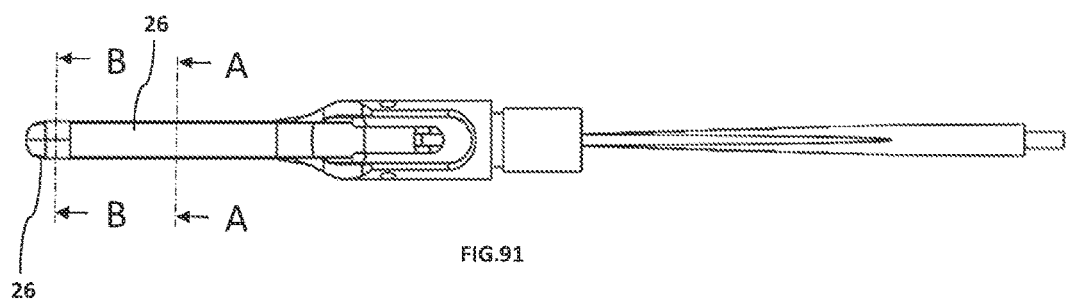
FIG.91
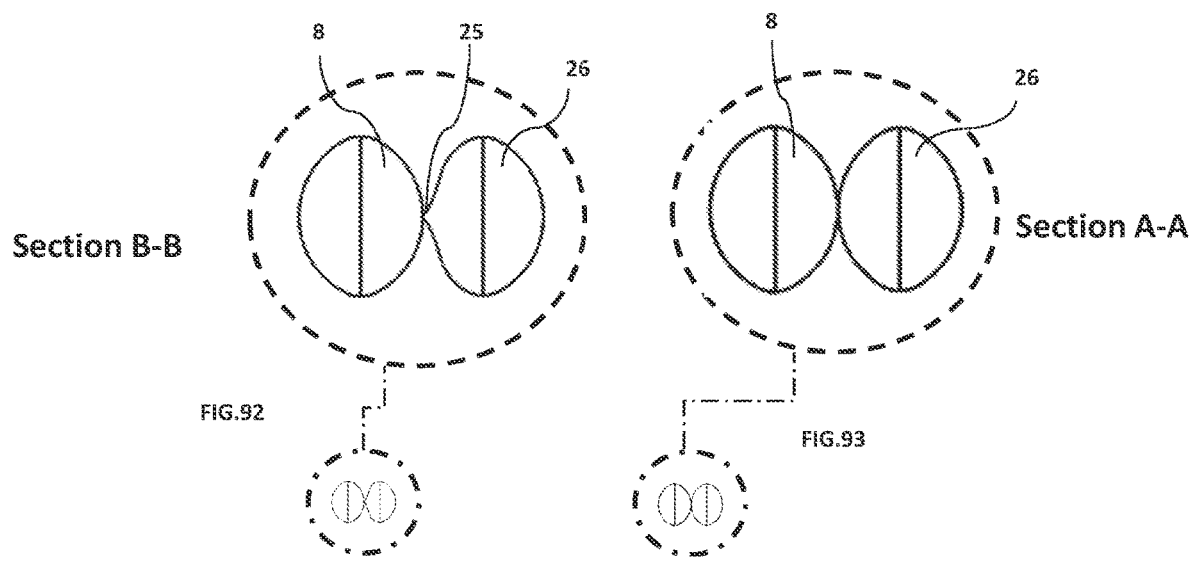
Section B-B
FIG.92
Section A-A
FIG.93

Detail 'X'

Section A-A

Section B-B

Section A-A

Section B-B

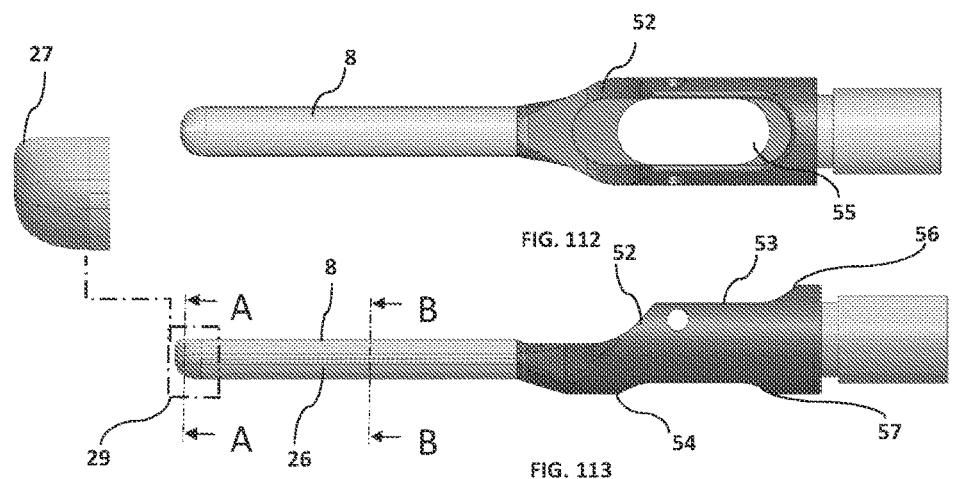
FIG. 112
FIG. 113
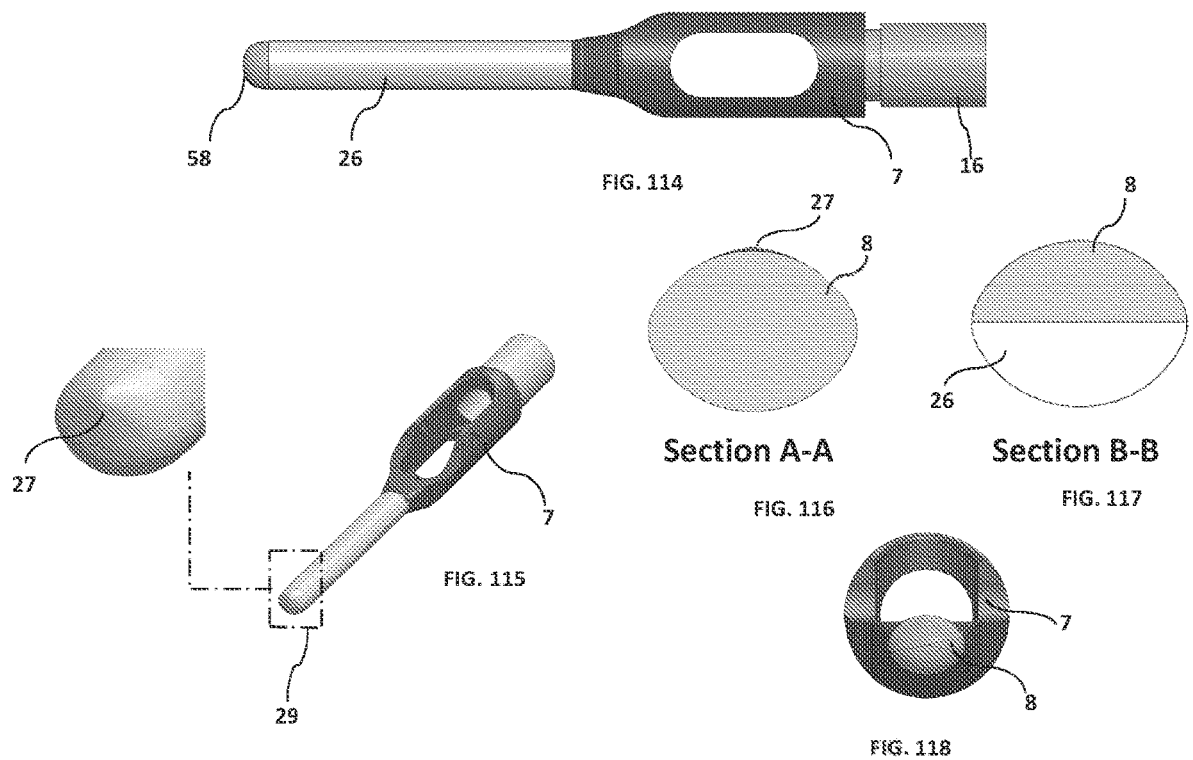
FIG. 114
FIG. 115
Section A-A
FIG. 116
Section B-B
FIG. 117
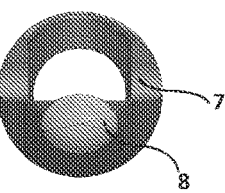
FIG. 118

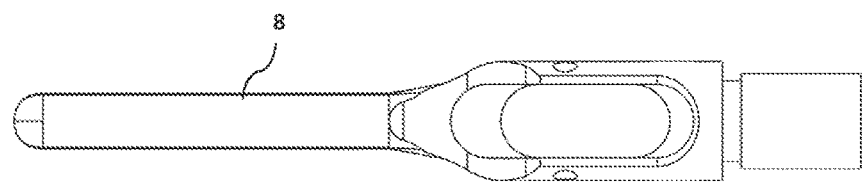
FIG. 119
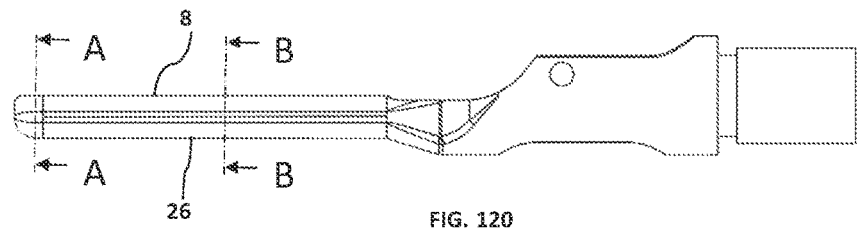
FIG. 120
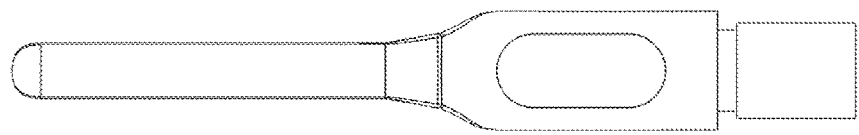
FIG. 121
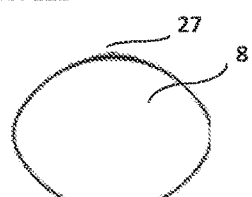
FIG. 122
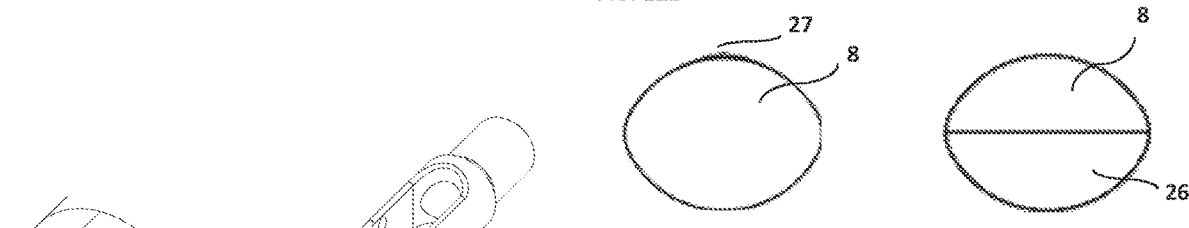
Section A-A
FIG. 123
Section B-B
FIG. 124
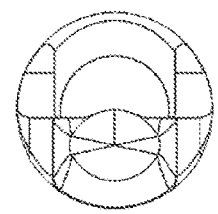
FIG. 125

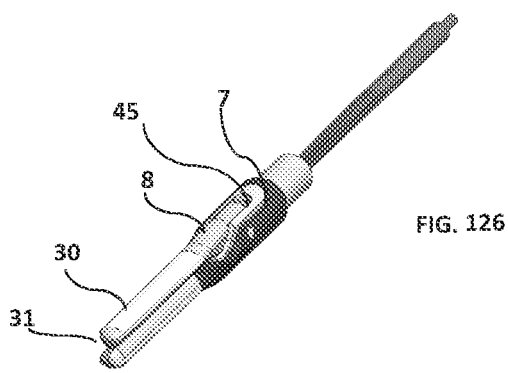
FIG. 126
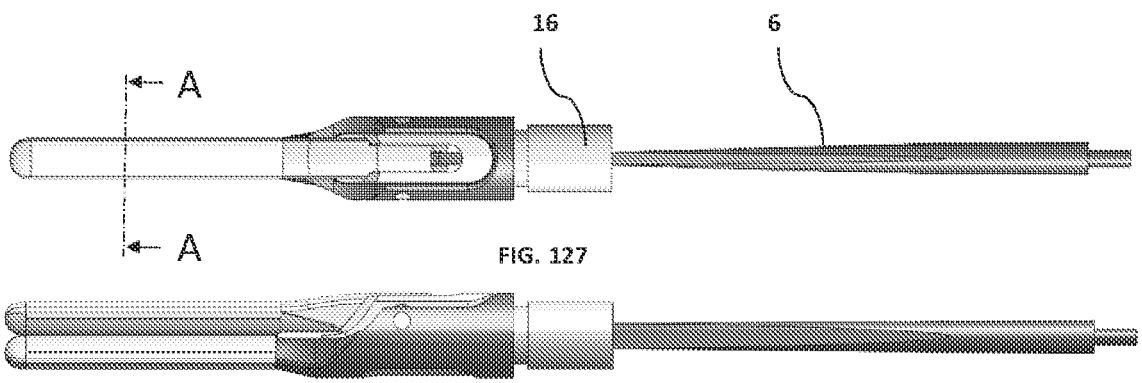
FIG. 127
FIG. 128
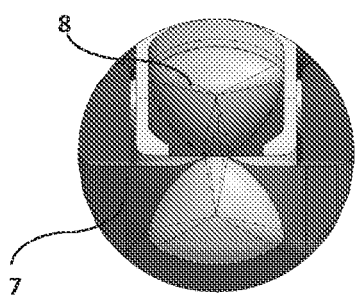
FIG. 129
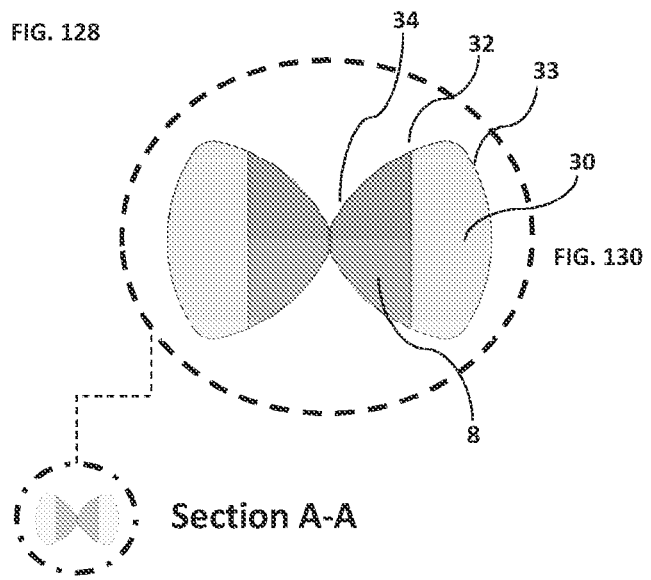
FIG. 130
Section A-A Section A-A

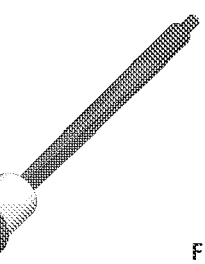
FIG. 136
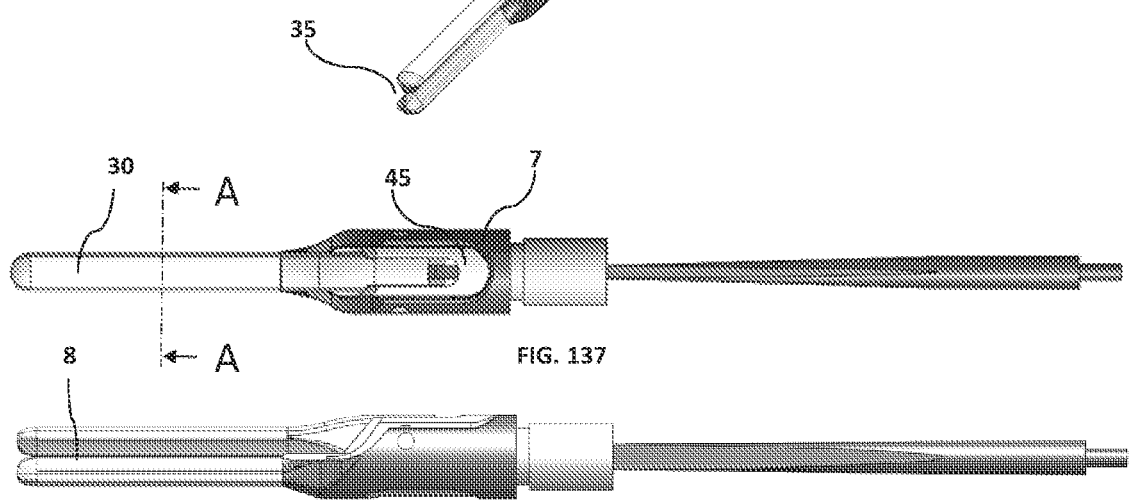
FIG. 137
FIG. 138
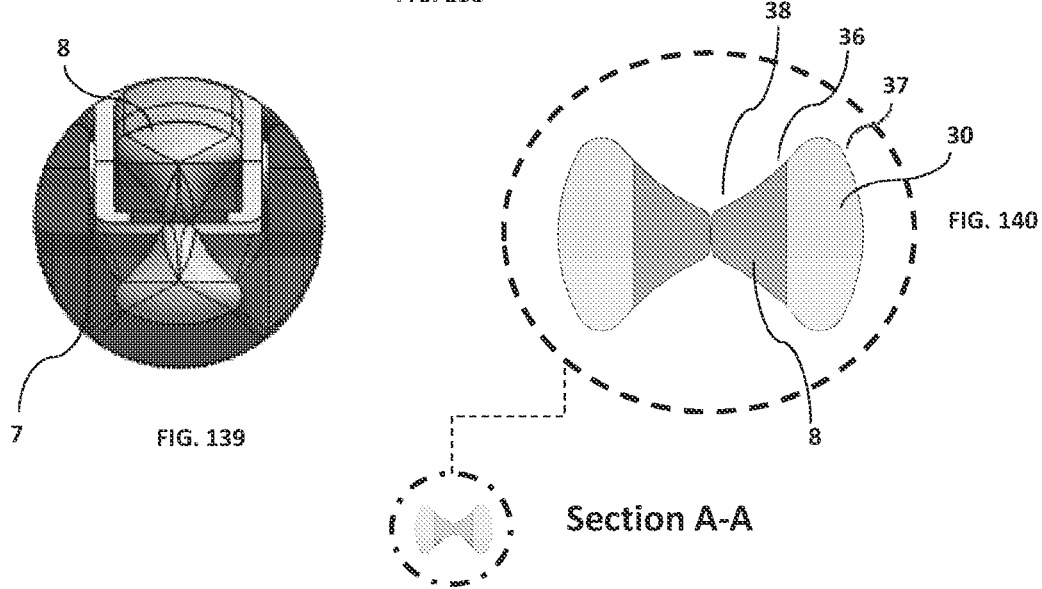
FIG. 139
FIG. 140
Section A-A Section A-A

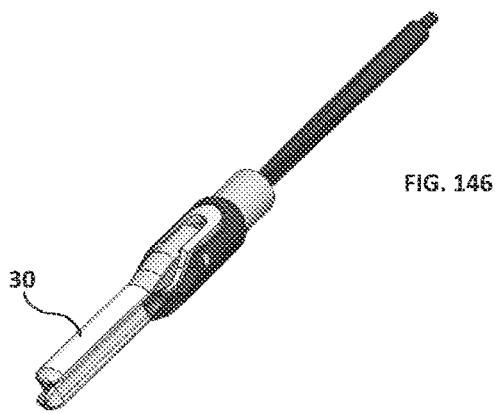
FIG. 146
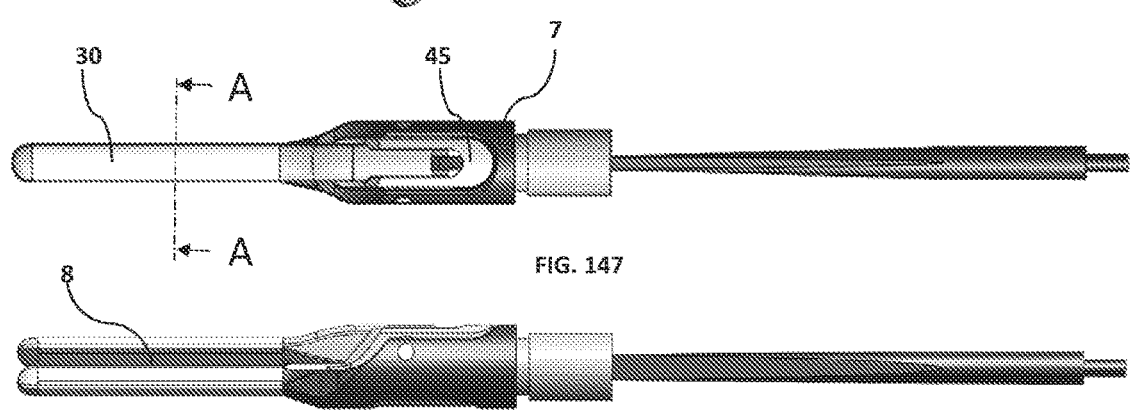
FIG. 147
FIG. 148
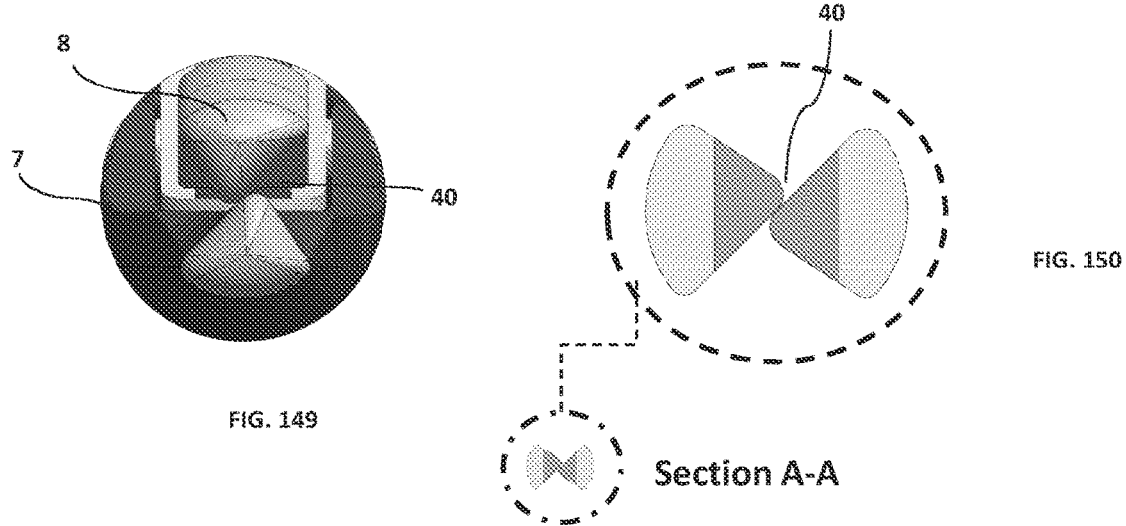
FIG. 149
FIG. 150
Section A-A Section A-A Section A-A Section B-B Section A-A   FIG. 163
Section B-B   FIG. 164

Section A-A

Detail 'X'

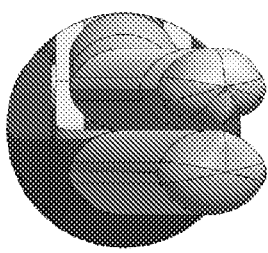
FIG. 171
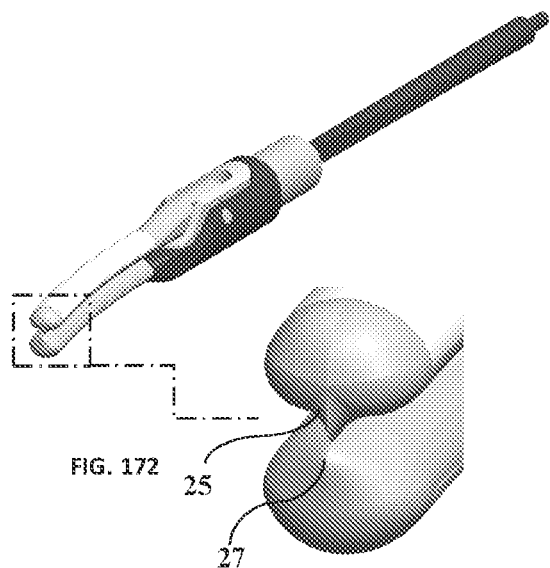
FIG. 172
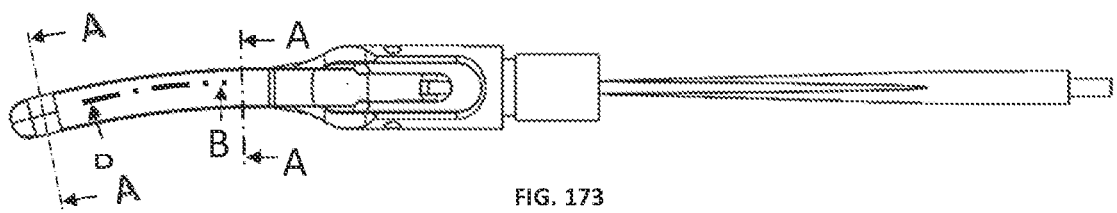
FIG. 173
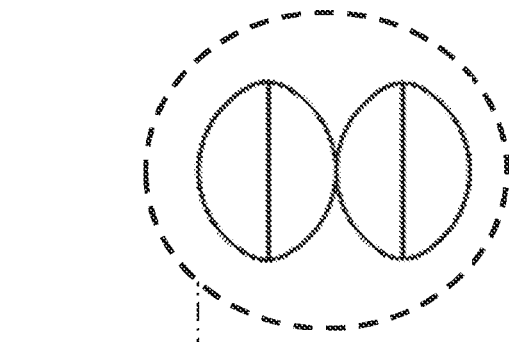
FIG. 174
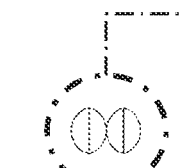
Section A-A 25
27

Detail 'X'

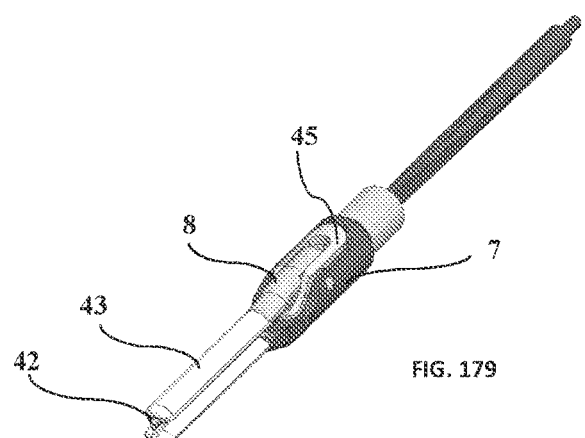
FIG. 179
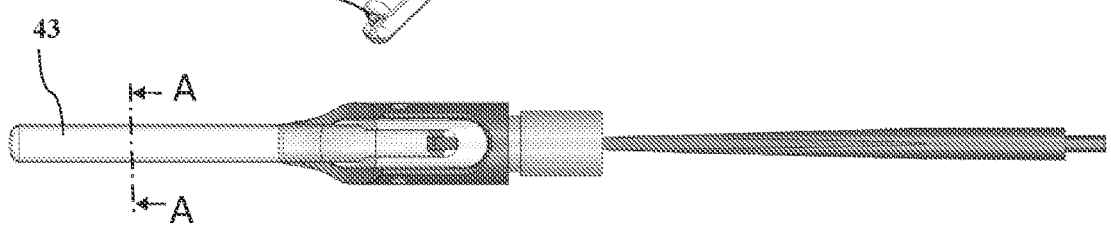
FIG. 180
FIG. 181
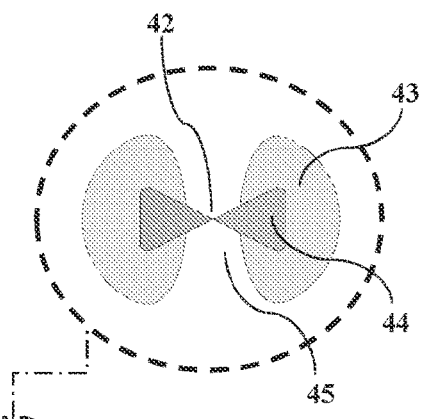
FIG. 182
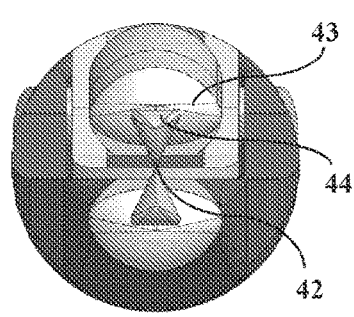
FIG. 183
Section A-A

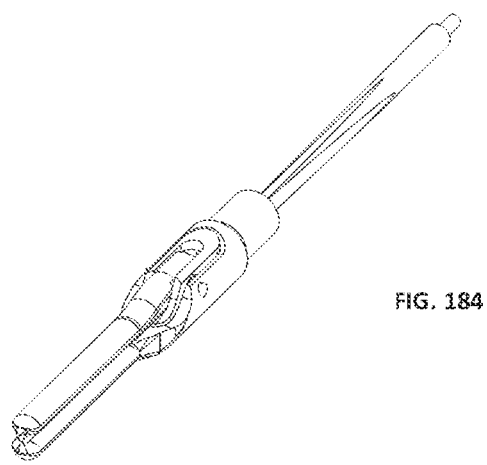
FIG. 184
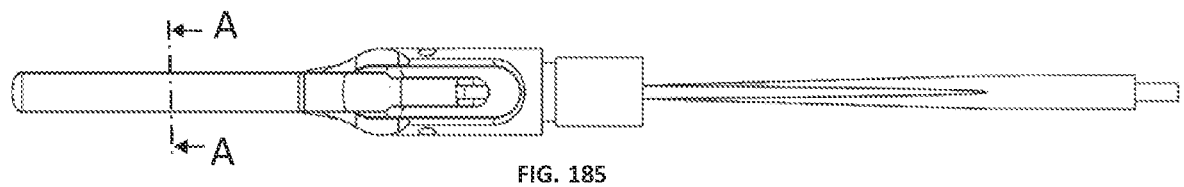
FIG. 185
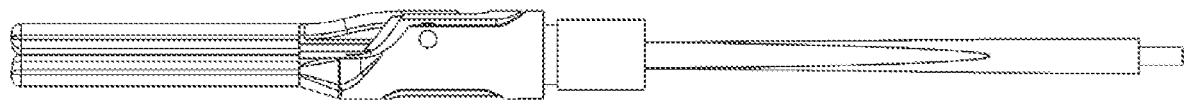
FIG. 186
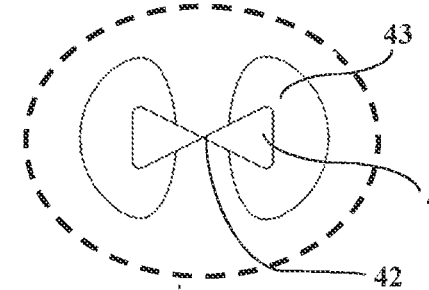
FIG. 187
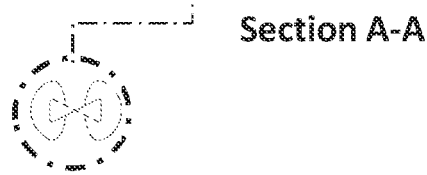
Section A-A
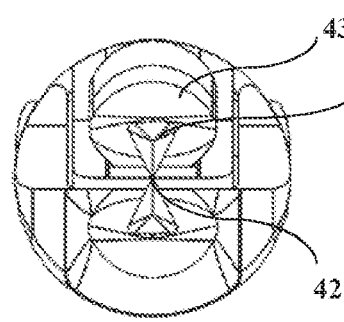
FIG. 188

Section A-A

Section A-A

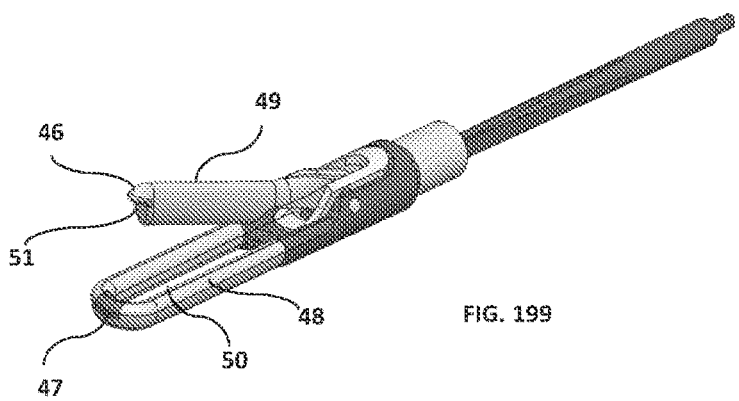
FIG. 199
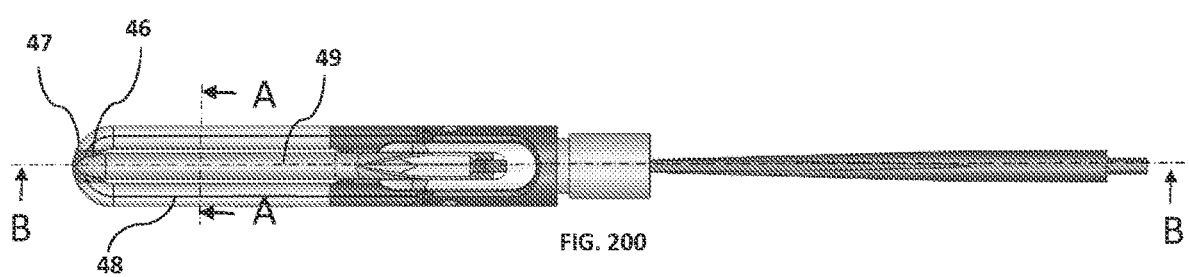
FIG. 200
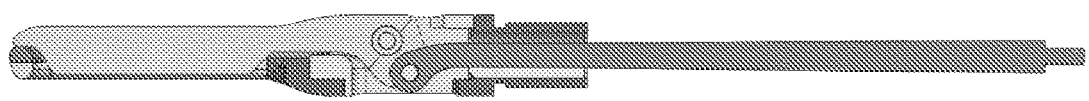
Section B-B    FIG. 201
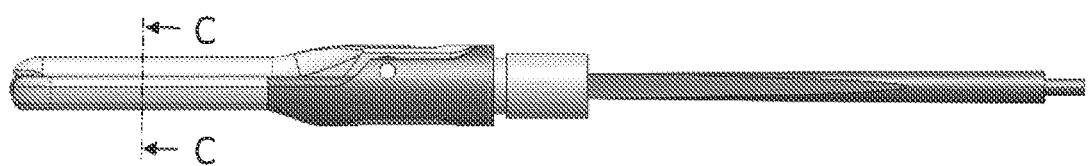
FIG. 202
Section C-C    FIG. 203
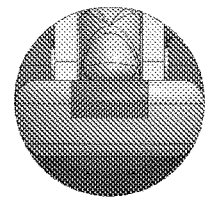
FIG. 204

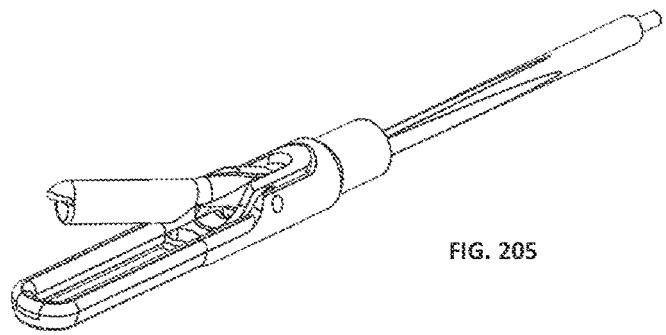
FIG. 205
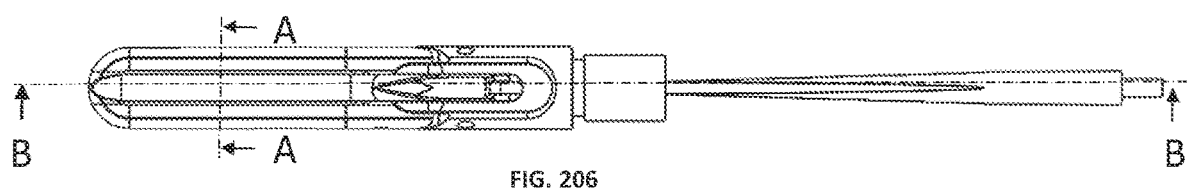
FIG. 206
FIG. 207  Section B-B
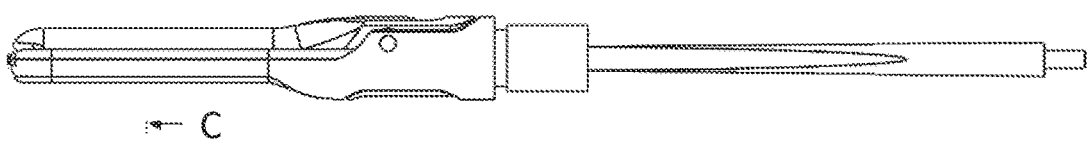
FIG. 208
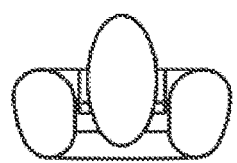
FIG. 209
Section C-C
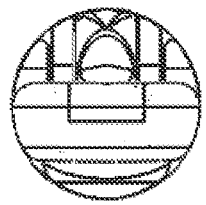
FIG. 210

TISSUE/VESSEL SEALER AND CUTTER WITH VARIABLE SHAPES OF JAW ASSEMBLY WITH PARTIAL DLC COATING

FIELD OF THE INVENTION

The present invention relates, in general, to a surgical instrument with vessel/tissue forceps and more particularly, to a surgical instrument having vessel/tissue sealer and/or cutter jaws designed with various shapes and more safer jaws whereby the jaws can be changed in the same instrument to allow a physician to seal and/or cut with ease and thereby improve proper handling, manipulation, sealing, cutting/transecting and segregating the vessel/tissue without change of instrument.

BACKGROUND

Arteries and veins form the network of blood supply. Arteries carry the oxygenated blood from the heart to the different organs at a certain pressure. Veins carry deoxygenated blood from the organs to the heart. Pressure of the blood flow in the arteries is higher than the veins.

Arteries have a different characteristic form according to their high pressure and dynamic action.

Veins have characteristic required for low pressure and large volume of deoxygenated blood.

During an organ removal surgery for any pathology requiring complete severance of the network of blood supply, it is necessary to seal (control/arrest blood flow) both the venous and arterial network connected to the target pathological organ.

"Vessel sealing" is defined as the process of liquefying the collagen, elastin and substances in the tissue so that the tissue reforms into a fused mass with significantly-reduced demarcation between the opposing tissue structures.

Sealing of the arteries differs from sealing of veins in terms of the power of the energy, time of application and form of the instrument performing the act.

Surgeons commonly face arterial and venous types of bleeding. A bleeding artery is high pressure, intermittently pulsating and muscular in nature.

Also some vessels are bare and covered with minimum fascia, while some are deeply embedded in tissue.

Various kinds of instruments have been used to seal and/or cut vessel/tissue in prior arts. There are various drawbacks that are encountered while using various such instruments for sealing and/or cutting and such instruments also face several problems such as extra power consumption if the jaws are wide and stout, lot of mechanical compressive strength has to be used by the surgeon. Force is required to seal and/or cut the vessel/tissue in retractile action.

There is charring and sticking of tissue if the current is not properly dispersed through the jaws. There is heating of the jaws. There are chances of short circuits leading to sparks, which is hazardous to patient safety.

By the very nature of the present design these drawbacks are overcome, wherein the force application is eliminated, making the device more hemostatic, safe, more effective, and causing less fatigue to the surgeon and achieving a precise sealing and/or cutting/shearing.

OBJECT OF THE INVENTION

Taking into consideration the above drawbacks of various instruments, the object of the invention is to provide a surgical instrument with jaws to reduce the surface area of contact to the tissue when the tissue is sealed and/or cut.

Another object of the invention is to reduce the required hemostatic energy to optimum to create sealing and to therefore create safer sealing at optimum without much burning of vessel/tissue.

Yet another object of the invention is the ability to achieve arterial and venous hemostasis without the change of instrument.

Yet another object of the invention is to achieve the "start to seal" cycle faster, so that there is less vessel/tissue damage around target area. This means that when the advanced vessel/tissue sealing energy is activated or when vessel sealing is to be achieved, the jaws of the sealer start heating up and seal the vessels. By virtue of the design of invention, the time required to achieve the sealing effect is reduced, hence less energy is used, leading to sealing faster, causing less spread to "untargeted" areas.

Yet another object of the invention is that the shearing/cutting effect should start after the seal has been achieved.

Yet another object of the invention is the ability to achieve precise cutting after sealing without the change of instrument.

Yet another object of the invention is to reduce sparks where there is conduction of current at common meeting point of current poles at the jaws creating sparks.

Yet another object of the invention is to provide super insulation properties thus safeguarding tissue in contact with the outer surface, which is not required to be sealed and/or cut.

Yet another object of the invention is to reduce sticking and charring of the vessel/tissue.

Another object of the invention is to reduce mechanical compressive strength and to reduce force during application of the instrument for sealing and/or transection/cutting after sealing.

One more object of the invention is to achieve equally potent safe arterial as well as venous vessel seal (hemostatic) effect as well as cutting effect with better segregation of surrounding tissues/vessels, for better surgeon control, to decrease surgical fatigue, to reduce surgical time, to increase patient safety, to decrease thermal dissipation around the target vessel/tissue.

One more object of the invention is to allow smooth segregation and moving or pushing away of the vessel/tissue preventing unnecessary breaking of the vessel/tissue thus making the procedure safe by preventing excess blood loss and atraumatic.

Yet another object is to increase versatility of the instrument to make it as much as ideal for even more complex surgeries like cancer surgeries requiring removing lymph nodes around large arterial and venous vessels.

SUMMARY OF THE INVENTION

The present invention describes a surgical instrument with a tissue/vessel sealer and/or cutter and various jaw assemblies with various shapes of the jaws where the jaws can be changed by the surgeon to provide safe and precise tissue/vessel sealing and/or cutting/shearing mechanisms by the jaws at the precise location and also help in better segregation of surrounding tissue/vessel away from the target tissue/vessel and therefore avoiding burning or charring of healthy tissue thereby preventing any extra cutting where it is not required or intended and further enhancing sharp cutting at the desired location for removal of tissue/vessel during surgery.

The geometry of the jaws is to enable variety of the shapes of the jaw to be used by changing the jaw assemblies by detaching the rod from the housing as per requirement by the surgeon and to extend its utility for laparoscopic, minimally invasive, conventional (laparotomy) surgeries, open surgery, and robotic surgery.

By introducing various shapes and geometries of the jaw forms, working around the same principle of sealing and/or shearing/cutting tissue at precise locations, sharp secure cutting with lesser strokes, and fewer traumas to the patient can be achieved.

The geometry of the jaws can be extended to be used in different angulations like straight jaw, curved jaw or any form or combination of all these and can be of different lengths.

The principle of partial diamond like coating (DLC), optionally a ceramic insert plus TiN coating (titanium nitride coating) on the jaws made of steel is used in this invention in the jaw assembly for achieving super insulation properties achieved by partial DLC coating and optional ceramic insert, while non-sticking and non-charring of the tissue is achieved by the TiN coating on the steel jaws.

In further embodiments diamond like coating will be illustrated as DLC and titanium nitride will be illustrated as TiN.

Insulation is provided with partial DLC coating 7 in a patterned manner or any shape, at the substantially back portion which is the second portion 200 of the jaw assembly 1. The pattern of partial DLC coating at the second portion 200 is more clearly illustrated in FIG. 111, 112, 113, where it illustrates the hollow open substantially central portion 55 for insertion of ceramic insert 45, and the pattern of DLC coating is sliding 52 in the front and straight 53 at the back with elevation 56 at further back on top side of jaw leaving a hollow substantially central portion for ceramic insert. The DLC coating is substantially straight 54 and has a small sliding 57 inwardly at the bottom side of jaw leaving hollow substantially central portion 55 for ceramic insert 45. The rest of the part of the jaw assembly 1 at the substantially front portion which is the first portion 100 is of TiN coating 8 and is conductive. The partial DLC coating 7 at the back portion prevents arising of sparks where the pole current of the poles of outer tube 16 and working rod connection 6 meet at the common point of the jaw assembly 1. Working rod connection has full DLC coating.

Optional ceramic insert, partial DLC coating on the substantially back portion and TiN coating is a combination in the jaw assembly 1 which increases its safety, performance and reusability compared to other existing jaws.

In an embodiment, partial DLC coating can also be used in an isolated form on the steel jaws without combination with Tin coating and without ceramic insert or optionally with ceramic insert. In an embodiment TiN can be used in isolated form without partial DLC coating.

In another embodiment, half side back insulation 14 is provided on the back side of at least one the jaw which can be provided to the various embodiments of the jaw so that the jaw is conductive on the front side/overlapping portion 8 which conducts current at a faster rate and the back insulation prevents the side or back tissue from current and at the same time the back side of the jaw is cold when there is no current and at the same time the jaw is conductive at a faster rate due to thin conductive front part 8 made of TiN coating.

The jaws can be single action jaw where one jaw is moving and one jaw is fixed, or it can be double action jaw where both the jaws are moving.

BRIEF DESCRIPTION OF DRAWINGS

FIGS. 3-12 illustrates the narrow base jaws with partial diamond like coating (DLC); optionally a ceramic insert plus TiN coating (titanium nitride coating).

FIGS. 30-39 illustrates the substantially elliptical jaws.

FIGS. 56-65 illustrates elliptical jaws with substantially half side back insulation.

FIGS. 66-82 illustrates grasp projecting edges/ridges and groove on both the jaws with substantially half side back insulation.

FIGS. 83-97 illustrates one jaw with sharp pointed projection and another with elevated portion with substantially half side back insulation.

FIGS. 112-125 illustrates fixed jaw with elevated portion.

FIGS. 126-135 illustrates concave shape jaws with substantially half side back insulation.

FIGS. 136-145 illustrates convex shape jaws with substantially half side back insulation.

FIGS. 146-155 illustrates criss-cross concave or convex jaws with substantially half side back insulation.

FIGS. 156-166 illustrates curved jaw with grasp projecting edges/ridges and groove on both the jaws with substantially half side back insulation.

FIGS. 167-178 illustrates curved jaw with one jaw having sharp pointed projection and another having elevated portion with substantially half side back insulation.

FIGS. 179-188 illustrates embedded sealer/cutter inside the insulated portion in the jaws with substantially half side back insulation till the tip.

FIGS. 199-210 illustrates jaws with pointed beak like tip, and another jaw has a U shaped jaw having hollow space in the centre with insulation on substantially the tip.

DETAILED DESCRIPTION

The present invention describes a tissue sealer and/or cutter with various jaw assemblies to provide safe tissue/vessel sealing and/or cutting mechanism allowing proper handling with the jaw such that the tissue/vessel is safely and precisely sealed and/or cut at the area and therefore avoiding unintended burning of healthy tissue thereby preventing any extra cutting and further enhancing sharp cutting at the desired location for removal of tissue during surgery. It can also cause coagulation or desiccation of vessel/tissue.

The geometry of the jaws is to enable variety of the shapes of the jaw to be used by changing the jaw assemblies by detaching the rod 2 from the housing as per requirement by the surgeon or to extend its utility for laparoscopic, minimally invasive, conventional (laparotomy) surgeries, open surgery, and robotic surgery.

In all the embodiments that are illustrated below, the jaws can be single action jaw where one jaw is moving and one jaw is fixed, or it can be double action jaw where both the jaws are moving. The rod 2 can be fully rotated to change the position of the jaws during surgery.

It has been observed in previous existing jaws that if they are wide and stout, cause lot of mechanical compressive strength to be used by the surgeon and lot of power consumption. Force is required to seal and/or cut the vessel/tissue in retractile action in such jaws.

In various embodiments below, various jaw designs, shapes and geometries have been incorporated to provide better sealing and/or cutting overcoming the drawbacks of existing jaws.

The principle of the geometry of the jaws is to enable various shapes/geometries of the jaws to be used or to extend its utility for laparoscopic, minimal invasive, and conventional (laparotomy) surgeries, robotic surgeries without any limitations. Extending this geometry to be used in different angulations like straight jaw, curved jaw or any form or combination of all these and can be of different lengths.

The various shapes of the jaw described in various embodiments particularly also allows smooth segregation and moving or pushing away of the vessel/tissue that are not intended to be sealed and/or cut preventing unnecessary breaking of the vessel/tissue thus making the procedure safe by preventing excess blood loss and atraumatic.

Figure 1:
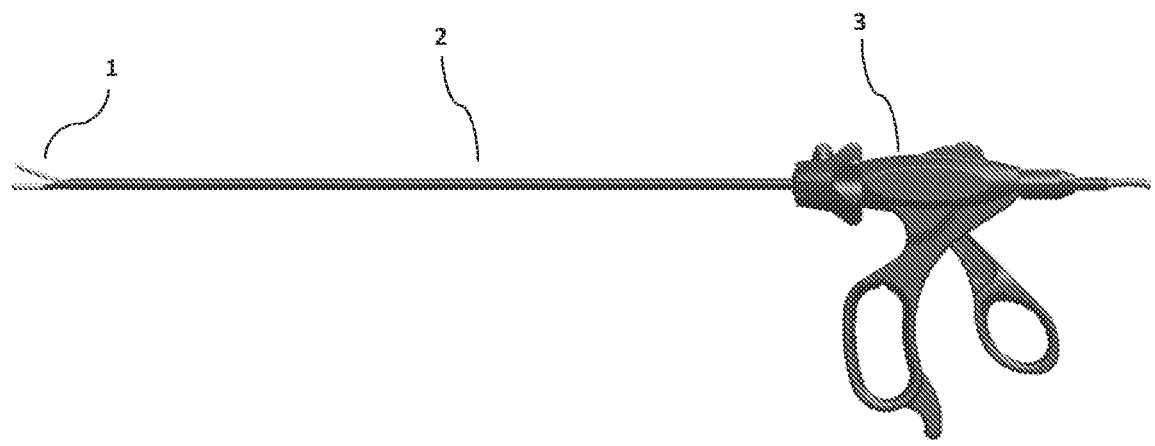
FIGS. 1-2 illustrates the vessel/tissue sealer and/or cutter instrument.
Figure 2:

FIG. 1 and FIG. 2 illustrates the entire device of the laparoscopic sealer and/or cutter wherein it has a jaw assembly 1, long rod 2 and rod connector housing 3 for connection of the long rod 2 which is detachable from the housing 3 if the surgeon requires to change the jaws thereby allowing changing in the same instrument. In an embodiment, the jaws can also be changed by detaching the jaw assembly only rather than detaching the long rod 2.

Various jaw assemblies are provided in the invention for achieving targeted, safe and precise sealing and/or cutting of vessel/tissue such that the vessel/tissue is perfectly sealed quickly at first before sharply cutting without damaging the healthy tissue.

As illustrated in FIG. 3, FIG. 5, FIG. 6 and FIG. 8, FIG. 10, FIG. 11, the mechanism of jaw assembly 1 works on a hinge point 9 wherein the working rod connection 6 provides current to the moving jaw 4 and outer tube 16 provides current to the fixed jaw 5 simultaneously. There is TiN coating 8 on the conductive first portion 100 at the substantially front portion of the jaw assembly 1.

For the current to pass through the conductive parts of the jaw assembly, the pole wire from the cable is transferred inside the rod connector housing 3 which transfers the current to the outer tube 16 which in turn is connected and transfers the current directly to the fixed jaw 5 and has a direct pole while the current from the working rod connection 6 is transferred to the moving jaw 5 having pole with second current.

At the point of connection of current at common point sparks arise. To avoid this, the jaw assembly is coated with partial DLC coating Tat the substantially back portion which is the second portion 200 in a patterned manner. Both the outer tube 16 and the working rod connection 6 are insulated. The outer tube 16 is insulated by fixing the long rod 2 with treaded attachment to the outer tube 16 and the working rod connection 6 is insulated by providing an insulated coating with full DLC coating on it. The pattern of partial DLC coating 7 can be of any form, area, pattern and shape.

There is insulation provided with partial DLC coating 7 in a patterned manner or any shape, at the substantially back portion which is the second portion 200 of the jaw assembly 1 where there is common meeting point between the pole which gives current to the outer tube 16 and the pole which gives current to the working rod connection 6, so that there are no electric sparks where the working rod connection 6 and outer tube 16 pole current meets providing a safer jaw assembly when the current is further transferred to the moving jaw 4 and fixed jaw 5. Due to the partial DLC coating 7, there is TiN coating 8 on the other parts where there is no partial. DLC coating on the jaw assembly 1.

Figure 111:
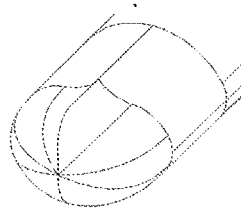

The pattern of partial (diamond like coating) DLC coating at the second portion 200 is more clearly illustrated in FIG. 111, 112, 113, where it illustrates the hollow open substantially central portion 55 for insertion of ceramic insert 45, and the pattern of DLC coating is sliding 52 in the front and straight 53 at the back with elevation 56 further back on top side of jaw leaving a hollow central portion for ceramic insert. The DLC coating is substantially straight 54 and has a small sliding 57 inwardly at the bottom side of jaw leaving a hollow substantially central portion 55 for ceramic insert.

DLC is diamond like coating and TiN is titanium nitride coating. Diamond like coating will be illustrated as DLC and titanium nitride will be illustrated as TiN in further description and embodiments.

FIG. 5 and FIG. 10, illustrates the top view of the jaw assembly while FIG. 6 and FIG. 11 illustrates the front view of the jaw assembly wherein it clearly explains the partial DLC coating 7 in a patterned manner on the substantially back portion which is the second portion 200 of the jaw assembly 1 and conductive first portion 100 having TiN coating 8, at the substantial front portion. FIG. 7 and FIG. 12 illustrates the side view of the jaw assembly 1.

In an embodiment the DLC can be coated partially without ceramic insert on the substantially back portion.

Plastics used in currently used jaws expand and contract whenever there is heating and cooling cycles and can become loose and cause wear and tear due to high temperature, mechanical strength, and shocks.

Biomedical material such as ceramic which provides high amount of heat resistance and insulation property can be optionally inserted as a ceramic insert 45 within the partial DLC coating 7 at the substantially central position or on the peripheral position where the ceramic insert is bio friendly, withstands higher degree of temperature, mechanical pressure, force, shocks, and has higher dielectric strength and also can withstand repeated heating and cooling cycles better than the existing jaws.

This ceramic insert 45 used within partial DLC coating gives the jaws better integrity and mobility which is not given by plastics used in already existing jaws which tends to becomes loose and mal aligned during heating and cooling cycle. The plastic also gets worn out during other cleaning processes used by the surgeon to clean the jaws such as any sharp objects to remove debris stuck in the crevices of the jaws.

It can withstand repeated autoclave cycles because of solid strength and high dielectric properties. It has good blending properties than with DLC coating than plastic.

The principle of partial diamond like coating (DLC) in the back portion, optionally a ceramic insert 45 on the substantially central portion or peripheral position of the partial DLC coating, plus TiN coating (titanium nitride coating) on the jaws made of steel on the front portion is applied in this invention in the jaw assembly for achieving super insulation properties achieved by partial DLC coating and optional ceramic insert 45, while non-sticking and non-charring of the tissue is achieved by the TiN coating on the steel jaw assembly in the front portion and due to various shapes of the jaw assembly in the front portion described further. The jaws may also be made of any material other than steel.

Optional ceramic insert, partial DLC coating and TiN coating is a combination in the jaw assembly 1 which increases its safety, performance and reusability compared to other existing jaws. This kind of combination gives the jaws better integrity and mobility.

In an embodiment, partial DLC coating can also be used in an isolated form on the steel jaws without combination with Tin coating and without ceramic insert or optionally with ceramic insert. In an embodiment, TiN can be used in isolated form without partial DLC coating.

According to the operation action or the surgical requirement in the body the proportion or ratio of ceramic insert, DLC coating and TiN coating will change and is defined. For each device a specific threshold proportion would be defined based on the surgical procedure.

As shown in FIG. 4 and FIG. 9, this shape of the jaw allows the narrow base 11 of the jaw having lesser surface area at the base to target the located and desired vessel/tissue to be sealed and/or cut at the narrow base 11. The tissue held in the centre, where the inside surfaces of the jaws meet, is sealed and/or cut precisely, with lesser surface area, thereby enhancing the efficacy of the energy. The upper region 10 of the jaw is curved which tapers and aligns to form a narrow base 11 having lesser surface area.

In an embodiment, at least one jaw can have substantially half side back insulation 21 at the back side leaving an area of the tip and substantially near the tip region non insulated 58 as shown in FIG. 56.

This shape of the jaw allows expansion of tissue laterally, after the jaws are closed together. This reduces the diameter/thickness of the vessel/tissue compressed in the centre at the narrow base 11. This ensures compression, with faster penetration of current to achieve sealing. The form of the jaw prevents disruption of vessels. It enables smooth cutting action of the tissue/vessel after grasping and sealing.

The geometry of the jaws (the moving and fixed) are specifically designed for important features such as safety and efficacy. It is designed for atraumatic tissue grasping with sealing and/or cutting. There is less area of surface contact, minimal tissue damage on sealing. There is precise cutting/shearing of vessel by the advanced bipolar current without disturbing the seal created to occlude the vessel completely, thereby enhancing hemostatic efficacy.

The tip is designed to initiate the cutting and shearing action specifically after a completion of seal cycle, so as to prevent premature shearing at the time of sealing. The tip is also used to segregate and push the unwanted vessel/tissue preventing damage. The overall effect of sealing followed by cutting of vessel/tissue does not require delivery of pressure in the jaw by virtue of this design.

This design of the jaw and in all the designs illustrated below, allows achieving equally potent safe arterial as well as venous vessel seal (hemostatic) effect or tissue seal, to reduce surgical time, to increase patient safety, to decrease thermal dissipation around the target tissue. Force application is eliminated, which makes the device safe, more effective, less fatigue is required while using it by the surgeon and more hemostatic and precise shear is attained.

In another embodiment, there can be a TiN/Ag (TiN coating/Silver coating) in the conductive portion of the jaw assembly. The TiN/Ag will provide anti-microbial properties at the rate of approximately 99.99% to the jaw assembly at the conductive part. This property is mainly because of silver which acts as an antimicrobial agent.

Figure 13:
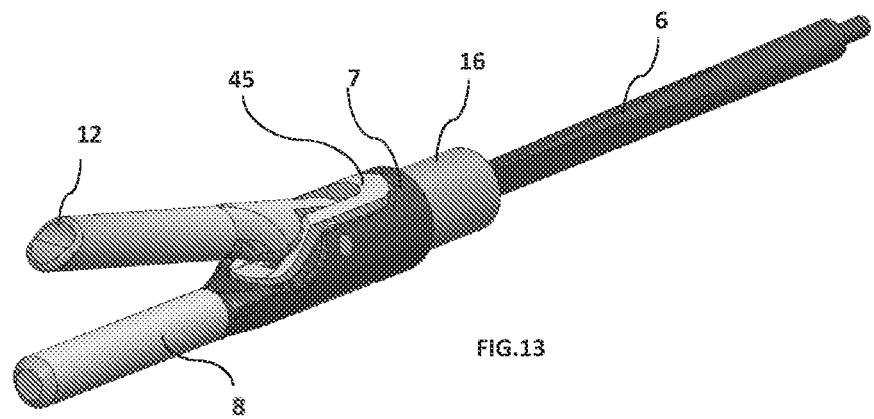
FIGS. 13-20 illustrates the jaws with tapered tip. (Dolphin nose jaws)
Figure 17:
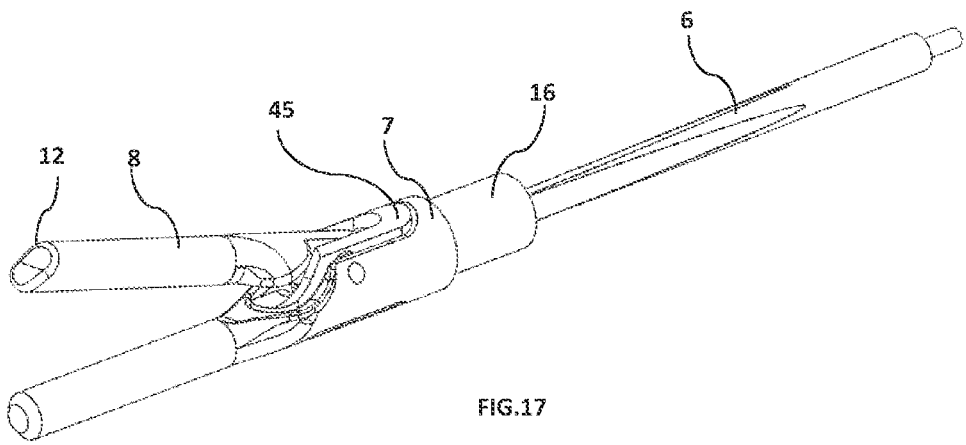

In an embodiment as illustrated in FIG. 13 and FIG. 17, the jaw is narrowed or tapered substantially at the upper part of tip 12 (dolphin nose) of at least one jaw (moving or fixed jaw) so that the jaw does not push the tissue and exactly targets and picks the vessel/tissue.

Figure 14:
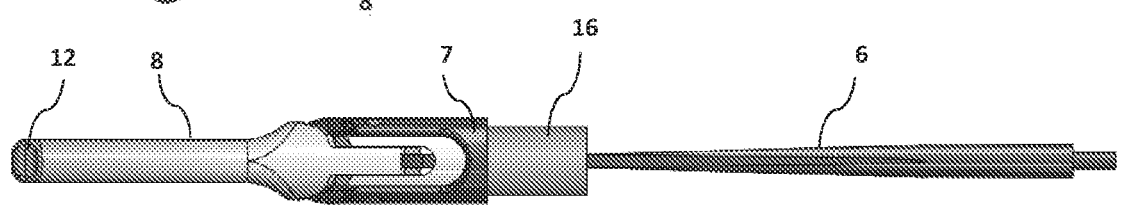
Figure 15:
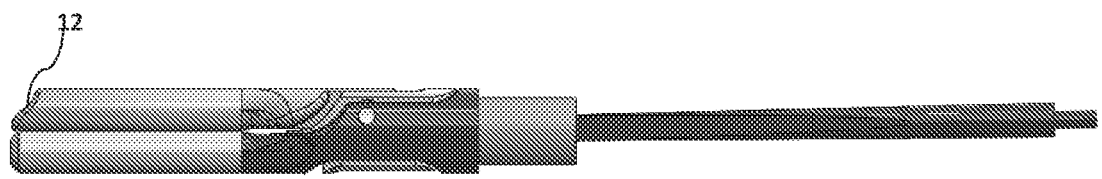
Figure 16:
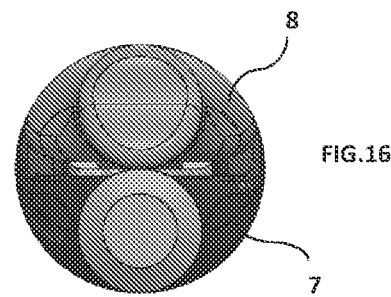
Figure 18:
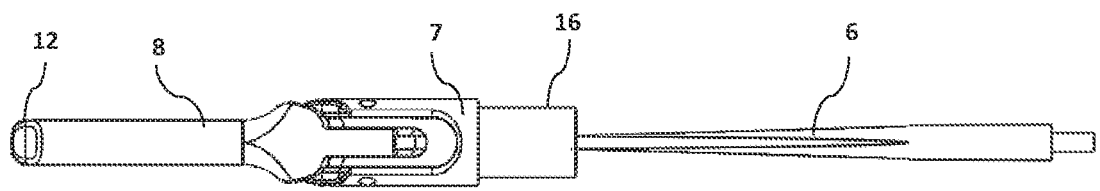
Figure 19:
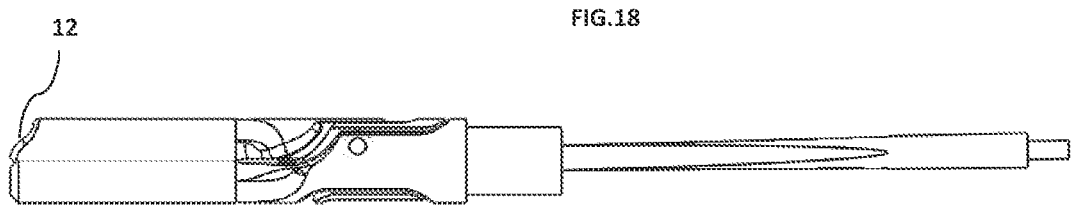
Figure 20:
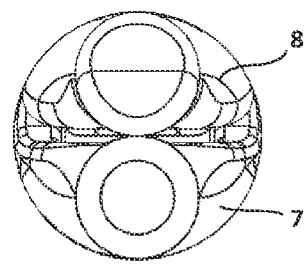

FIG. 14 and FIG. 18 illustrates the top view of this embodiment of jaw assembly, while FIG. 15 and FIG. 19 illustrates the front views of this embodiment, FIG. 16 and FIG. 20 illustrates the side views of this embodiment.

In an embodiment, at least one jaw can have substantially half side back insulation 21 at the back side leaving an area of the tip and substantially near the tip region non insulated 58 as shown in FIG. 56.

Dolphin nose tip offers advantage of cutting in a non-traumatic fashion. It allows tissue to be segregated and separated away from the target tissue. Target tissue means the tissue that has to be sealed and/or cut.

Figure 21:
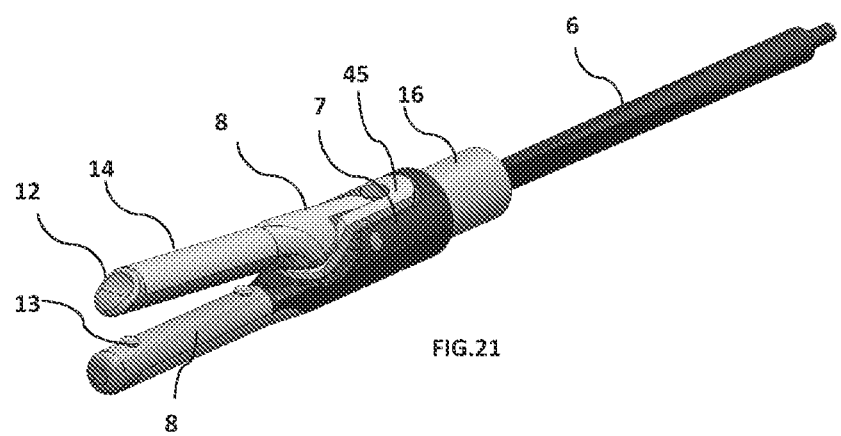
FIGS. 21-29 illustrates the tapered tip jaws with substantially half side back insulation.
Figure 26:
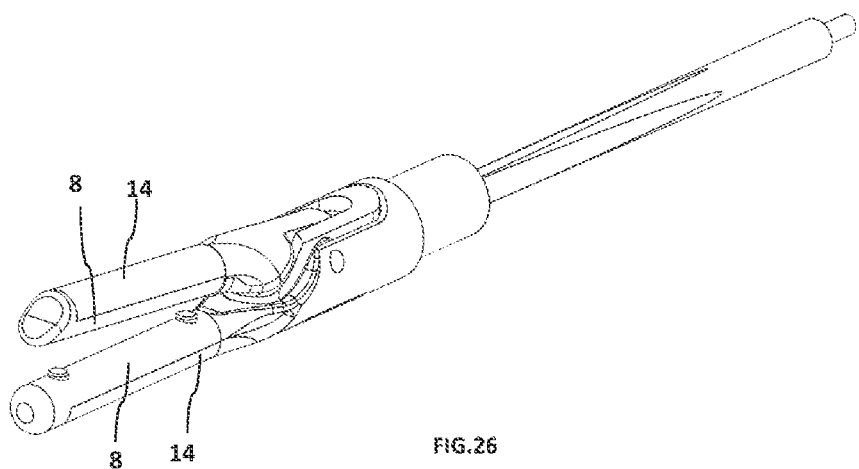

In another embodiment as illustrated in isometric view in FIG. 21 and FIG. 26, substantially half side back insulation 14 with DLC coating leaving an area of the tip and substantially near the tip region non insulated is provided on the back side of at least one of the jaws so that the jaw is conductive on the front side/overlapping portion which conducts current due to back insulation property at a faster rate and the back side insulation prevents the back vessel/tissue from current and at the same time causes the rod to cool down at a faster rate when there is no current and at the same time the jaw is conductive at a faster rate due to thin conductive front side/overlapping portion having TiN coating 8.

The jaw can be coated or attached to the conductive front/overlapping part 8 by various ways such as delrin molding, ceramic molding or DLC coating. There are stoppers 13 to stop the jaw from pressing further into tissue.

Figure 22:
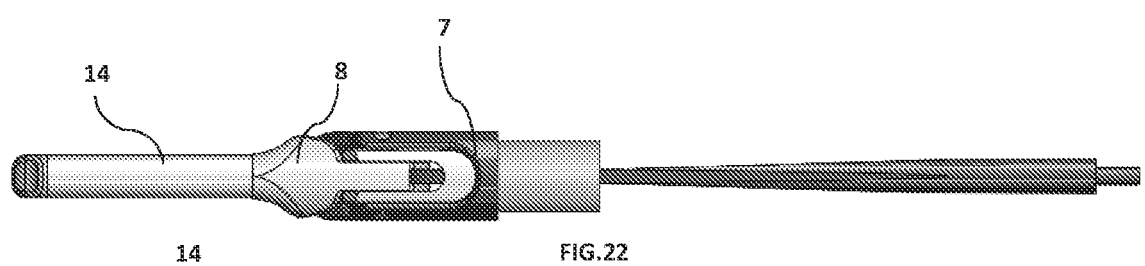
Figure 23:
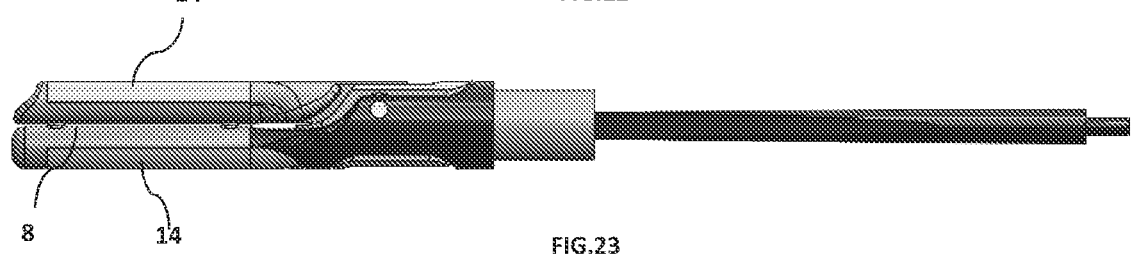
Figure 24:
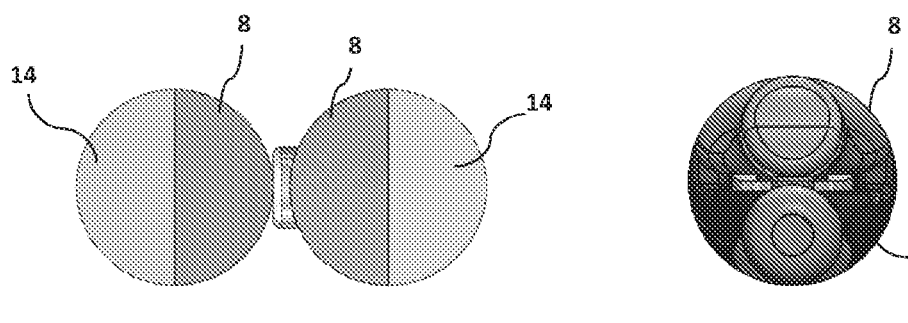
Figure 25:
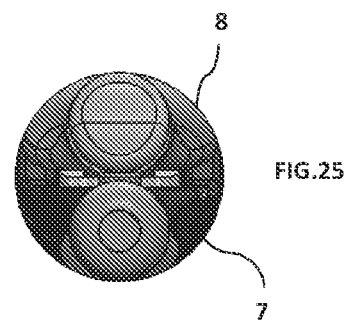
Figure 27:
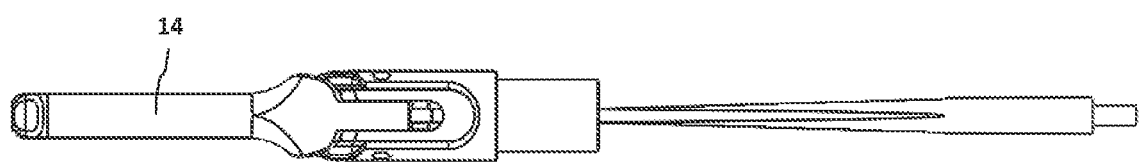
Figure 28:
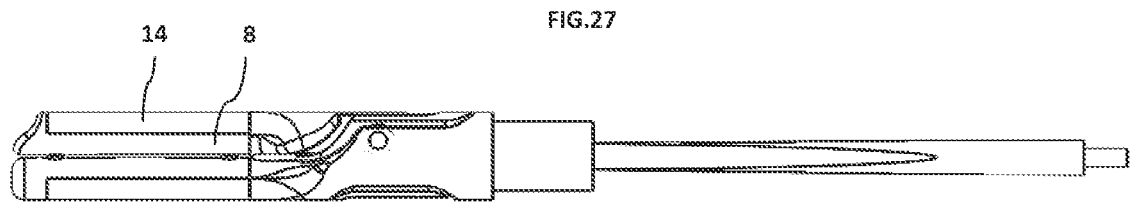
Figure 29:
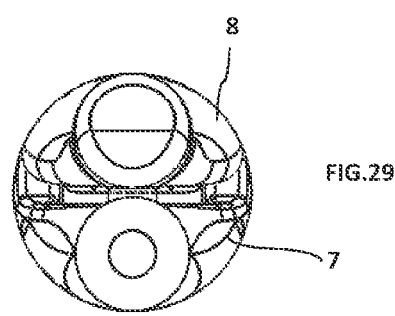

FIG. 22 and FIG. 27 illustrates the top view of this embodiment of jaw assembly with conductive front part/overlapping portion 8 and substantially half side back insulation 14 while FIG. 23 and FIG. 28 illustrates the front view of the embodiment. FIG. 24 is a cross sectional view of the jaw showing conductive front part/overlapping portion 8 and substantially half side back insulation 14 with partial DLC coating. FIG. 25 and FIG. 29 shows the side views of the jaw assembly with TiN coating 8 and partial DLC coating 7.

The back insulation can optionally be used in various shapes and designs of the jaw which are further illustrated.

The insulated back side 14 prevents the tissue at the backside from burning where the jaw has to be used in deeper hidden tissue/vessel where there is less space, thus preventing unwanted and healthy tissue burning at the back of the jaw therefore concentrating the current at the front part/overlapping portion 8.

The back side 14 is cold when there is no current and at the same time the jaw is conductive at a faster rate due to thin conductive front part 8 made of TiN coating. Insulation at the backside gives freedom to use in places where the vital organs are in close proximity.

Figure 30:
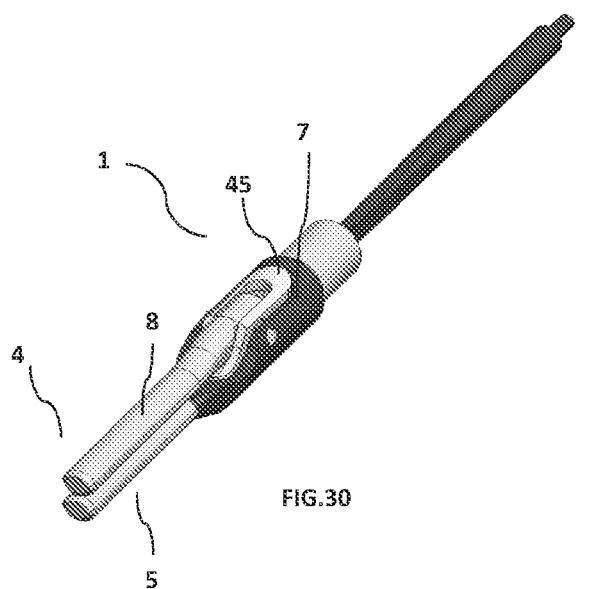
Figure 31:
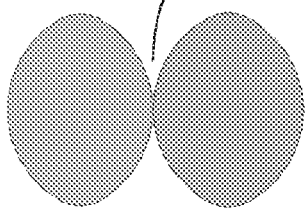

FIG. 30 and FIG. 35 illustrates isometric view where it displays the substantially elliptical curve shape of the jaws. The ellipse curve 15 is as shown in FIG. 31 and FIG. 36 which is the cross sectional view of the jaw assembly.

Figure 32:
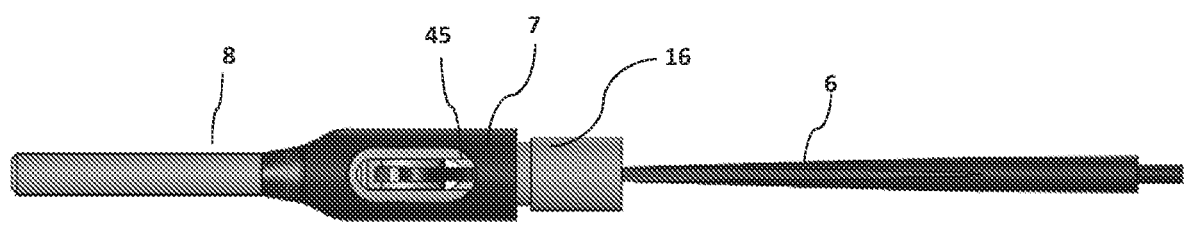

As shown in FIG. 32 which illustrates the top view, there is TiN coating 8 on the conductive first portion 100 of the jaw assembly. There is insulation provided with partial DLC coating 7 at the second portion 200 of the jaw assembly 1 where there is contact of the working rod connection 6 and outer tube 16 pole currents so that there are no electric sparks where the working rod connection 6 and outer tube 16 pole currents meet. There is optionally a ceramic insert 45 at the substantially central position within the partial DLC coating 7 or at peripheral position of the partial DLC coating 7.

Figure 33:
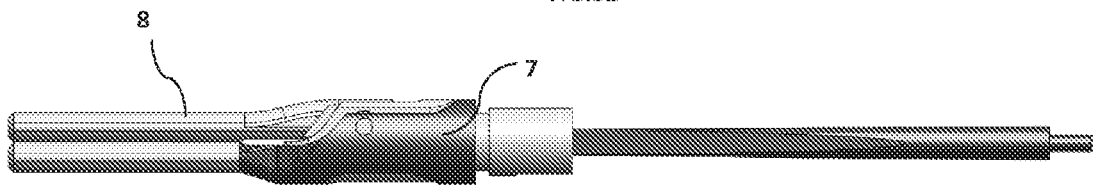
Figure 34:
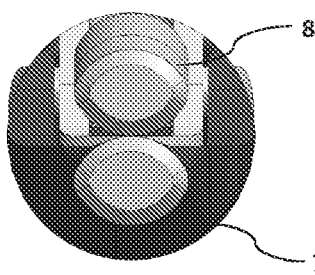

FIG. 32 and FIG. 38 illustrates the top view of this embodiment of jaw assembly, while FIG. 33 and FIG. 37 illustrates the front view of this embodiment, FIG. 34 and FIG. 39 illustrates the side views of this embodiment, showing TiN coating 8 on the conductive first portion 100 of the jaw assembly 1. There is insulation provided with partial DLC coating Tat the substantially second portion 200 of the jaw assembly 1.

In an embodiment, at least one jaw can have substantially half side back insulation 21 at the back side leaving an area of the tip and substantially near the tip region non insulated 58 as shown in FIG. 56.

Ellipse depicts human fingers. Before the advent of instruments, and even in routine surgery fingers are used efficiently. Elliptical shape offers atraumatic property to cut the tissue compared to existing designs. The smooth elliptical (finger-like) jaw shape has reduced surface area thus concentrating the current at the target without greater dispersion of current, thereby reducing the power and heat damage without compromising sealing.

Figure 40:
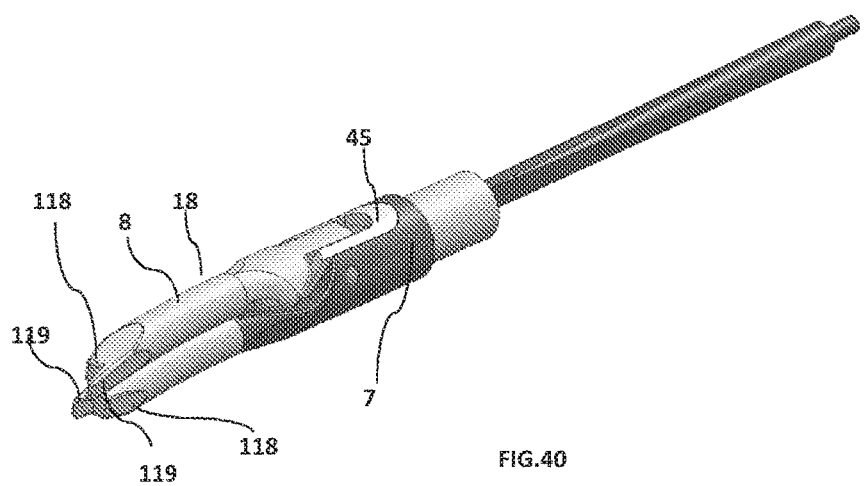
FIGS. 40-47 illustrates jaws with curved shape with extended longer part and shorter part in zig zag shape.
Figure 44:
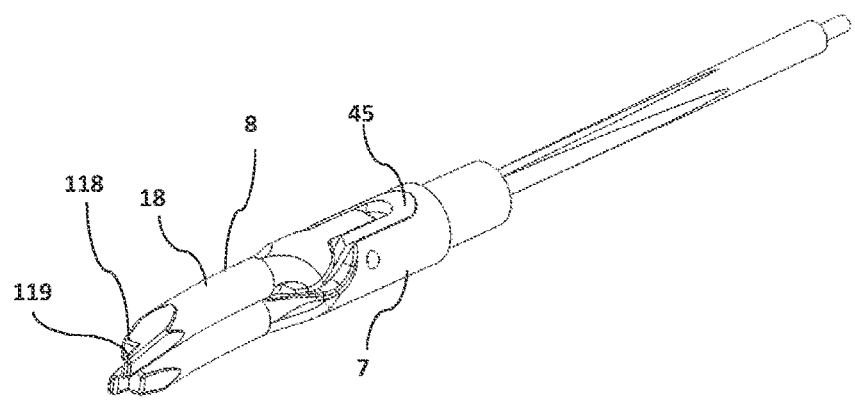

In an embodiment as illustrated in FIG. 40 and FIG. 44, the jaw can be having curved shape 18 with extended longer part 118 and shorter part 119 in zigzag shape at the outer part or tip of at least one jaw and where the extended longer part 118 and shorter part 119 of both the jaws are in opposing direction facing each other laterally at the outer part or at the tip region with partial DLC coating Tat the second portion 200 on the jaw assembly and optionally a ceramic insert at the substantially central position within the partial DLC coating 7 or at peripheral position of the partial DLC coating 7.

Figure 41:
Figure 42:
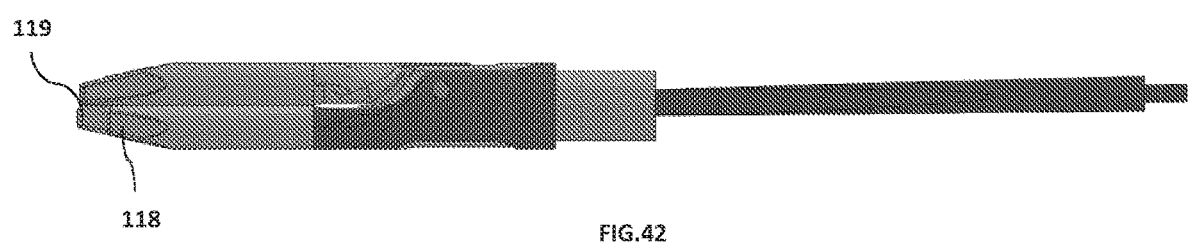
Figure 43:
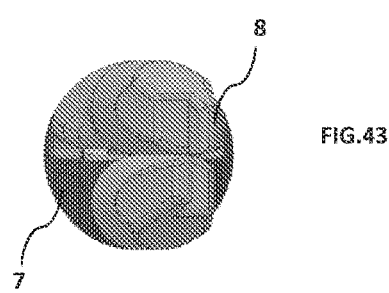
Figure 45:
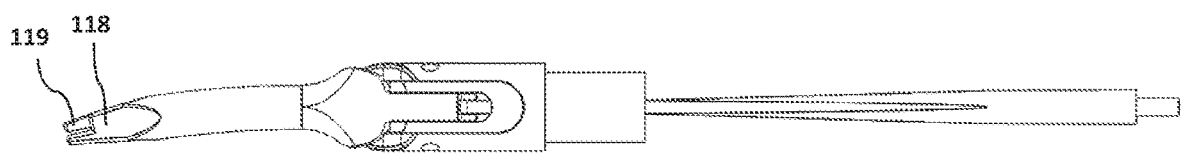
Figure 46:
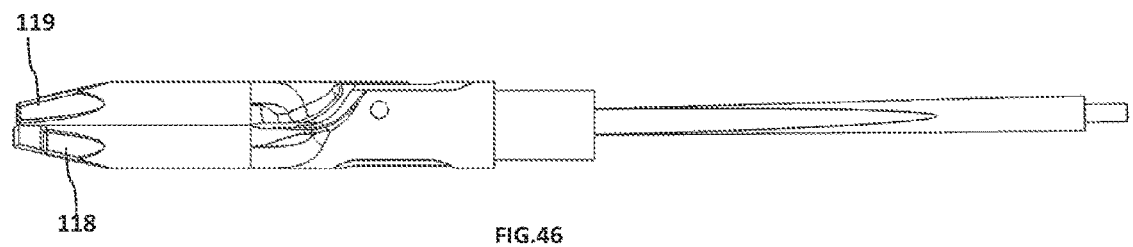
Figure 47:
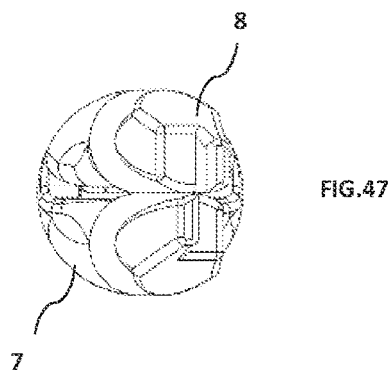

FIG. 41 and FIG. 45 shows the top view of this embodiment, while FIG. 42 and FIG. 46 shows the front view of the jaw assembly. FIG. 43 and FIG. 47 shows the side view curved shape 18 with extended longer part 118 and shorter part 119 in zigzag shape at the outer most part or tip region which is conductive and DLC coated 7 second portion 200 which is nonconductive for sealing and cutting.

In an embodiment, at least one jaw can have substantially half side back insulation 21 at the back side leaving an area of the tip and substantially near the tip region non insulated 58 as shown in FIG. 56.

The tip region can seal and/or cut in specific situations where vessel/tissue are small and covered by tissue for example adhesions. The curve offers versatility to enter in deeper spaces such as in hidden or deep in fascia covered locations and the extended longer upper part 118 and shorter lower part 119 of both the jaws in opposing direction provide easy grip of the tissue wherever it is so required during surgery.

Figure 48:
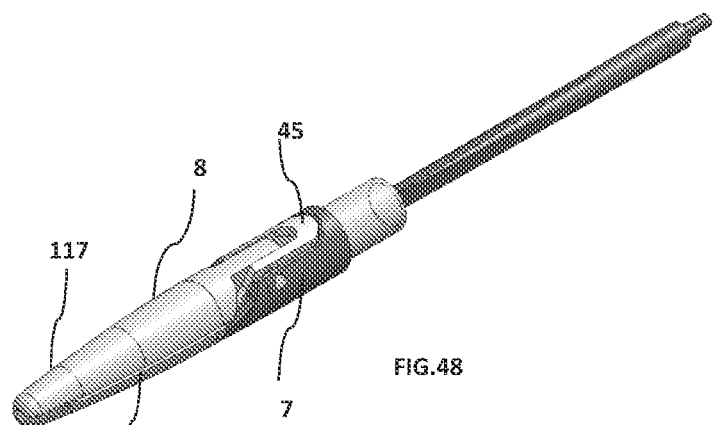
FIGS. 48-55 illustrates jaws with flat bottom portion and rounded tapered portion with serrations at the outer portion or at the tip. (Snake mouth jaws)
Figure 52:
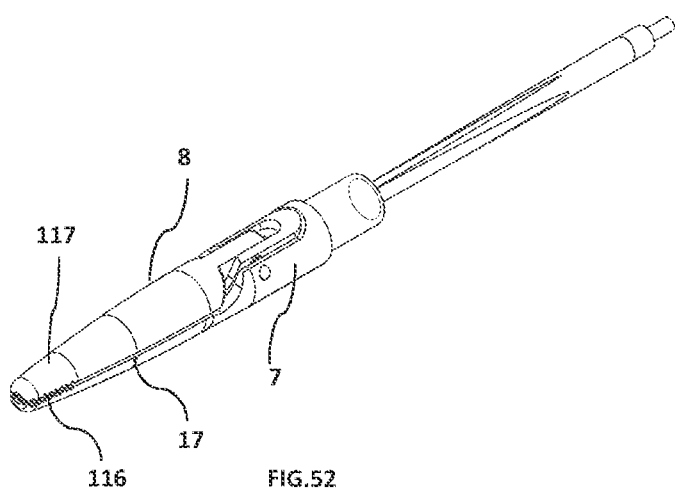

In an embodiment as illustrated in FIG. 48 and FIG. 52, in the isometric view, the jaw assembly can have substantially flat bottom portion 17 and rounded tapered portion 117 with serrations 116 at the outer portion of the jaw or at the tip on both moving jaw and fixed jaw for sealing purpose of artery/veins/tissue. There is partial DLC coating Tat the second portion 200 on the jaw assembly and optionally a ceramic insert 45 at the substantially central position within the partial DLC coating 7 or at peripheral position of the partial DLC coating 7.

Figure 49:
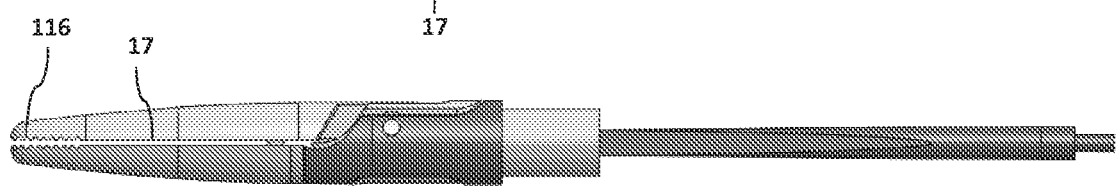
Figure 50:
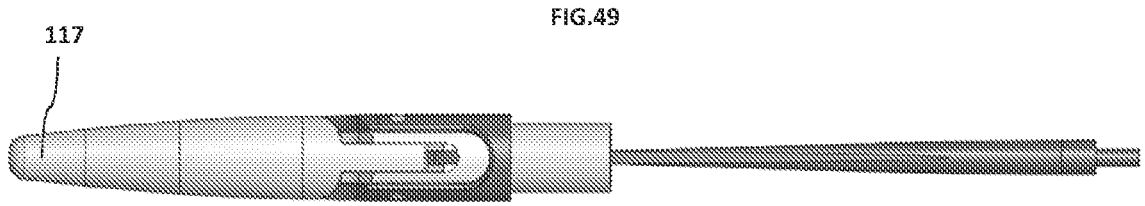
Figure 51:
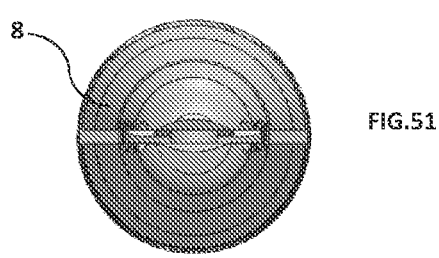
Figure 53:
Figure 54:
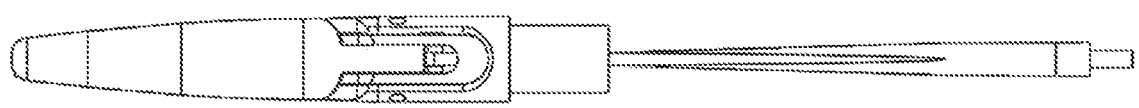
Figure 55:
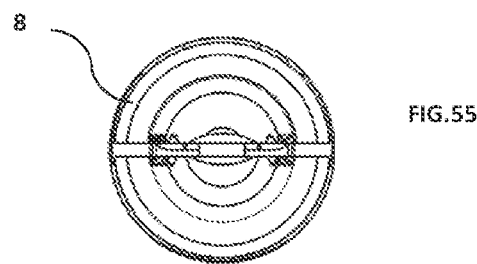

FIG. 50 and FIG. 54 shows the top view of this embodiment, while FIG. 49 and FIG. 53 shows the front view of the jaw assembly 1 with substantially flat bottom portion 17, conductive TiN coating 8 with rounded tapered portion 117 having serrations 116 at the outer portion or at the tip of at least one jaw and partial DLC coated 7 second portion 200. FIG. 51 and FIG. 55 shows the side view with conductive TiN coating 8.

In an embodiment, at least one jaw can have substantially half side back insulation 21 at the back side leaving an area of the tip and substantially near the tip region non insulated 58 as shown in FIG. 56.

In an embodiment, both the jaws can be moving instead of one fixed jaw and one moving jaw.

Figure 61:
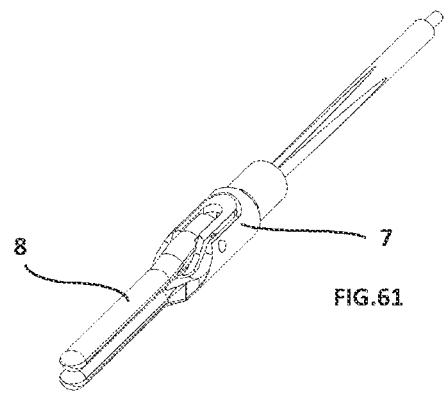

The above design of the jaw allows achieving arterial or venous vessel seal (hemostatic seal) or tissue seal. It offers grip for shorter pedicles like round ligament such as ovarian ligament due to serration at the tip. It also gives deeper sealing for thick tissue. Due to the round taper tip which is like the shape of snake mouth, the jaw pushes the vessel/tissue away smoothly and in atraumatic manner without breaking the vessel/tissue preventing when not required excess blood loss In another embodiment, FIG. 56 and FIG. 61 illustrates the isometric view, having one fixed jaw 5 and one moving jaw 4, which is a single action jaw, where the jaw assembly consists of TiN coating 8 on the conductive substantially front portion which is the first portion 100 of the jaw assembly and insulation is provided with partial DLC coating 7 at the substantially back portion which is second portion 200 of the jaw assembly 1 and optionally a ceramic insert 45 at the substantially central position within the partial DLC coating 7 or at peripheral position of the partial DLC coating 7. The jaw is substantially elliptical in shape.

Figure 62:
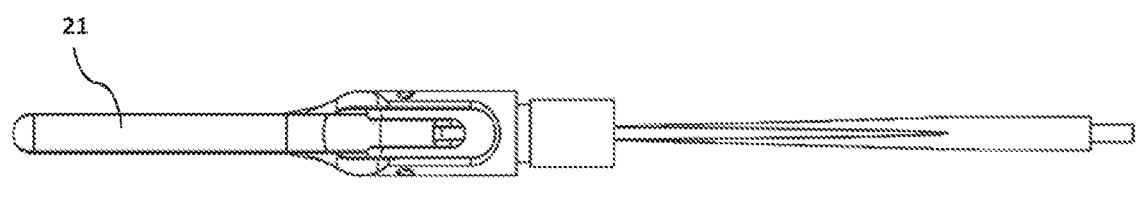
Figure 63:
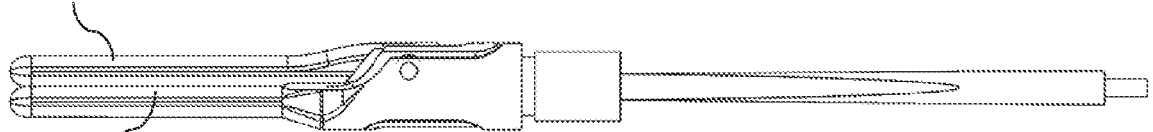

FIG. 57 and FIG. 62 is the top view showing insulation 21, and the jaws having elliptical shape 22. FIG. 58 and FIG. 63 illustrates the front view which shows the half side insulation 21 on the back side of at least one of the jaws leaving an area of the tip and substantially near the tip region non insulated 58, while the overlapping portions of the jaws consists of TiN coating 8 on the first portion 100 which is conductive. The TiN coating on the jaw allows for sharp conduction of current to seal and/or cut the vessel/tissue. While the partial DLC coating 7 on the second portion 200 of jaw assembly prevents sparks arising when two current poles of working rod connection band outer tube 16 meet.

Figure 64:
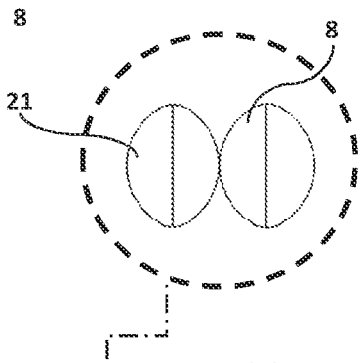
Figure 65:
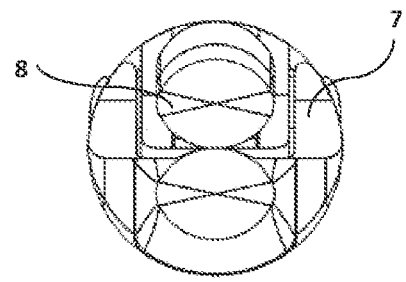

FIG. 59 and FIG. 64 is the sectional view of the jaws showing substantially half side insulation 21 and substantially half side TiN coating 8 while, FIG. 60 and FIG. 65 illustrates the side view of the jaw assembly. In an embodiment, both the jaws can be moving instead of one fixed jaw and one moving jaw.

Figure 66:
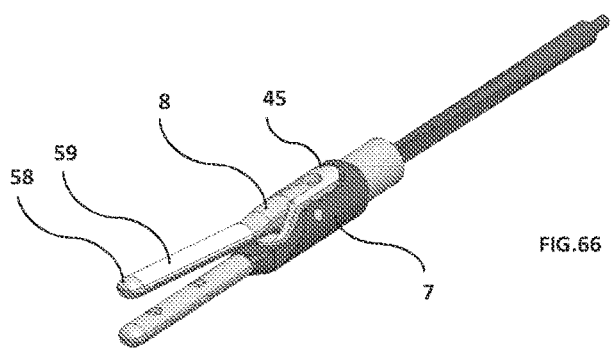

FIG. 66 illustrates the isometric view of the jaw assembly 1 (fixed jaw and moving jaw), working rod connection 6 and the outer tube 16.

Figure 67:
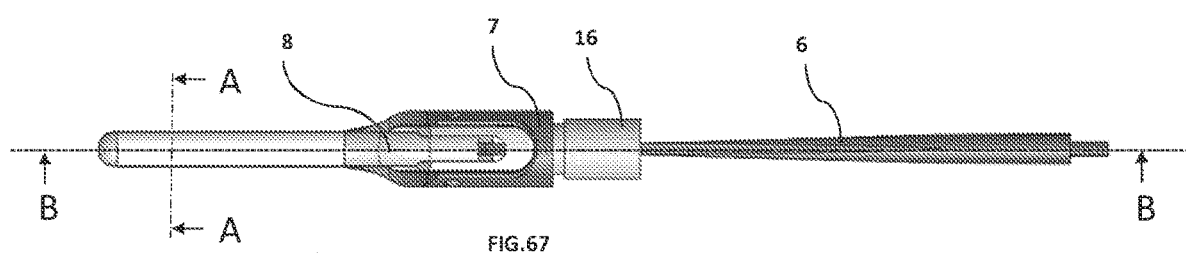

FIG. 67 and FIG. 75 illustrates the top view of the jaw assembly 1, working rod connection 6 and the outer tube 16, showing the moving jaw 4 with substantially half side insulation 59 at the back side of at least one jaw of the first portion 100 of the jaw assembly leaving an area of the tip and substantially near the tip region non insulated 58. There is partial DLC coating 7 at the second portion 200 and optionally a ceramic insert 45 at the substantially central position within the partial DLC coating 7 or at peripheral position of the partial DLC coating 7. It further shows the working rod connection 6 and the outer tube 16.

Figure 68:
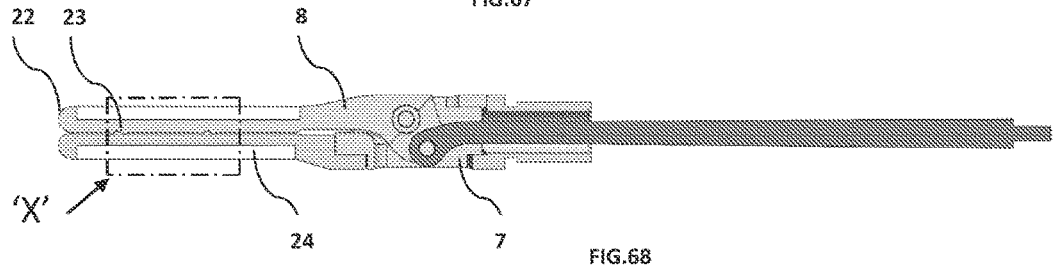
Figure 69:
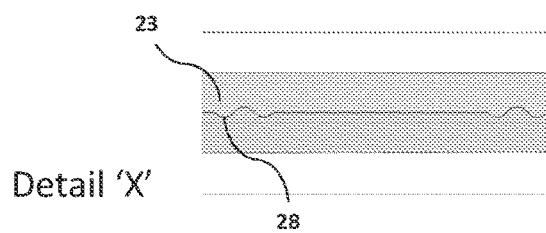

FIG. 68 and FIG. 76 illustrates the sectional view from FIG. 67 at axis B of the jaw assembly 1, working rod connection 6 and the outer tube 16, where the "detail X" shown in FIG. 69 and FIG. 77 shows the grasping and projecting edges/ridges 23 and groove 28 on the conductive overlapping positions on both jaws whereby the projecting edges/ridges present on both the jaws enter into the respective groove 28 present on both the jaws. The edges/ridges allow holding of the vessel/tissue tightly at one position and prevents slipping of vessel/tissue during sealing/cutting. These projections can be at intermittent positions or continuous on the jaw or any other part of the conductive portion of the jaws.

This shape of the jaw provides firmer grasp or grip with non-slippage. It ensures better surgical security. It enables a short sealing cycle.

FIG. 70 and FIG. 78 illustrates the front view of the jaw assembly (fixed jaw and moving jaw), working rod connection 6 and the outer tube 16, where there is TiN coating 8 on the substantially front conductive portion which is the first portion 100 of the jaw assembly and insulation is provided with partial DLC coating Tat the substantially back portion of jaw assembly 1 which is the second portion 200 of the jaw assembly 1 and optionally a ceramic insert 45 at the substantially central position within the partial DLC coating 7 or at peripheral position of the partial DLC coating 7.

Substantial half side insulation 24 is provided leaving an area of the tip and substantially near the tip region non insulated 58. There is partial DLC coating or any other material which can provide insulation on at least one jaw of the jaw assembly so that the tissues at the back of the jaws is protected.

FIG. 71 and FIG. 79 relates to FIG. 67 and FIG. 75 which illustrates the sectional view A-A of the jaws with substantial half side insulation 24 and substantial half side TiN coating 8.

FIG. 72 and FIG. 80 illustrates the side view of the jaws showing TiN coating 8 and partial DLC coating 7.

FIG. 73 and FIG. 81 illustrates the isometric view which also shows "detail view Y" in FIG. 74 and FIG. 82 of the jaw assembly, where it shows at least one of the jaws with substantially half side insulation 24 at back side leaving an area of the tip and substantially near the tip region non insulated and substantially half side TiN coating 8 which consists of grasp and projecting edges/ridges 23 and groove 28 on over lapping positions of both jaws into which the projecting edges/ridges enter into the respective groove 28 due to which tight grasping of vessel/tissue is achieved.

In another embodiment, both the jaws can be moving.

In an embodiment, only one jaw can have continuous or discontinuous edges/ridges, while the other jaw can have only the groove corresponding with those edges/ridges.

In another embodiment, FIG. 83 and FIG. 91 illustrates the top view of the jaw assembly 1, working rod connection 6 and the outer tube 16, and further showing the moving jaw 4 with substantially half side insulation 26 at the back side of the first portion 100 of at least one jaw of the jaw assembly leaving an area of the tip and substantially near the tip region non insulated 58 and partial DLC coating 7 at the second portion 200 of the jaw assembly and optionally a ceramic insert 45 at the substantially central position within the partial DLC coating 7 or at peripheral position of the partial DLC coating 7.

FIG. 84 and FIG. 92 along with FIG. 83 and FIG. 91 illustrates the sectional view B-B of the jaw, wherein the moving jaw has sharp pointed projection 25 at the substantially front edge or front part or front tip 29 so that it cuts tissue more prominently and sharply than other parts after grasping and sealing function is completed behind the tip region 29 of the jaw.

FIG. 85 and FIG. 93 along with FIG. 83 and FIG. 91 illustrates the sectional view A-A of the jaw, wherein there can be substantially half side insulation 26 and substantially half side TiN coating 8 for conducting current.

Figure 96:
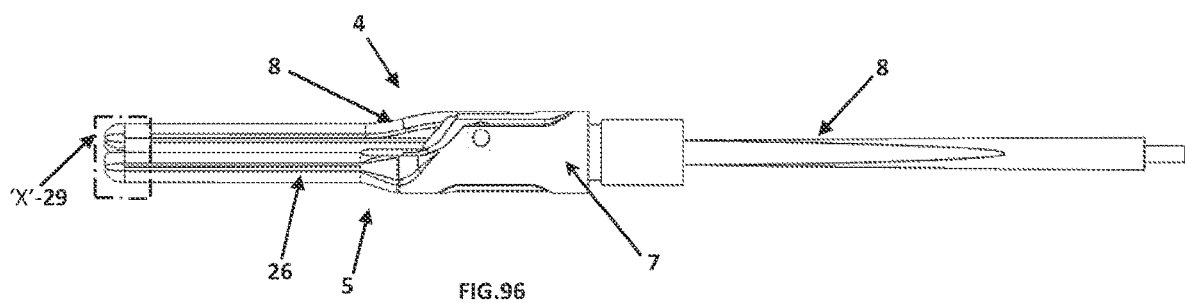

FIG. 86 and FIG. 96 illustrates the front view of the jaw assembly 1 with "detail X", working rod connection 6, outer tube 16, conductive first portion 100 having TiN coating 8 and DLC coating 7 at the second portion 200 and optionally a ceramic insert at the substantially central position within the partial DLC coating or at peripheral position of the partial DLC coating.

Figure 88:
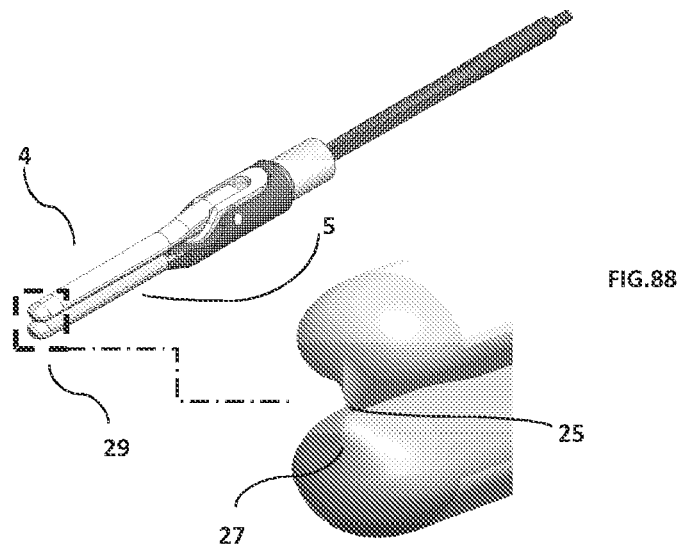
Figure 89:
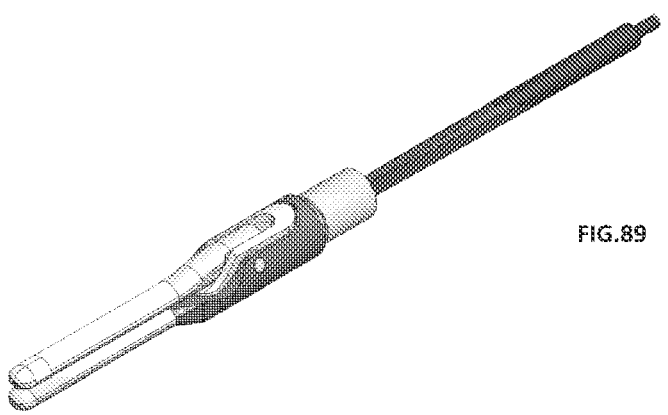
Figure 90:
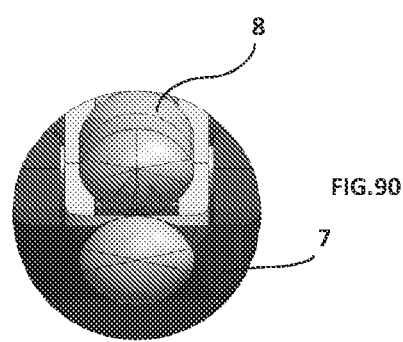
Figure 94:
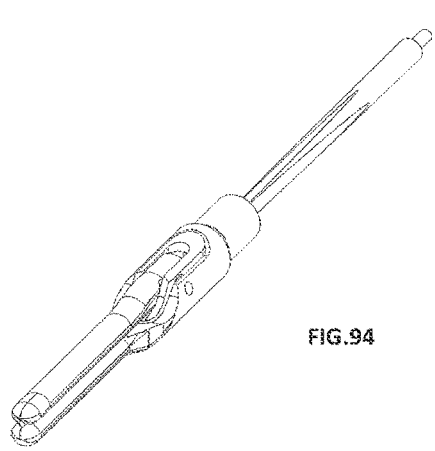
Figure 95:
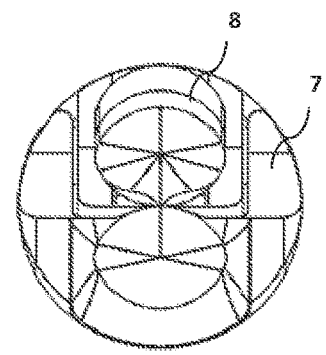
Figure 97:
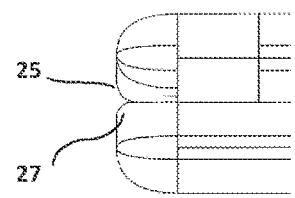

FIG. 87 and FIG. 97 shows the "detail X" illustrating the sharp pointed projection 25 from the front view and elevated portion 27 on the fixed jaw. FIG. 88, FIG. 89 and FIG. 94 shows the isometric view of the jaw clearly displaying the sharp pointed projection 25 at the substantially front edge or front part or front tip 29 (also shown as "detail X") of the moving jaw and elevated portion 27 on the fixed jaw. FIG. 90 and FIG. 95 shows the side view of the jaw assembly. In another embodiment both the jaws can be moving.

In another embodiment, the sharp pointed projection 25 can be on both the jaws.

In another embodiment, the sharp pointed projection 25 can be on fixed jaw and elevated portion 27 can be on moving jaw.

In another embodiment, the jaws can be without substantially half side insulation 30.

The jaws can be single action jaw where one jaw is moving 4 and one jaw is fixed 5, or it can be double action jaw where both the jaws are moving.

The portion behind the tip of the jaw is used for holding, grasping and sealing. The sharp pointed projection at the substantially front edge or front part or front tip later gives an advantage to deliver sharp current due to lesser surface area which cuts the tissue, so that the same instrument gives cutting function as a function of current with surgeon's control.

Figure 98:
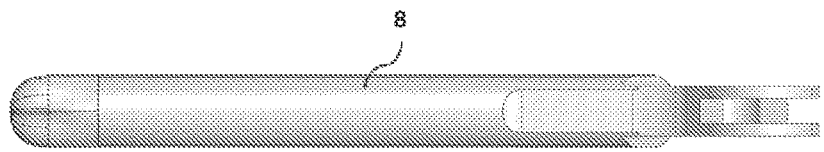
FIGS. 98-111 illustrates moving jaw with sharp pointed projection.
Figure 105:
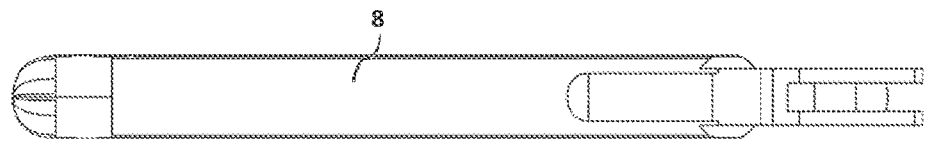

FIG. 98 and FIG. 105 illustrates the top view of the moving jaw 4 having pointed projection 25 at the substantially front edge or front part or front tip 29 of the jaw.

Figure 99:
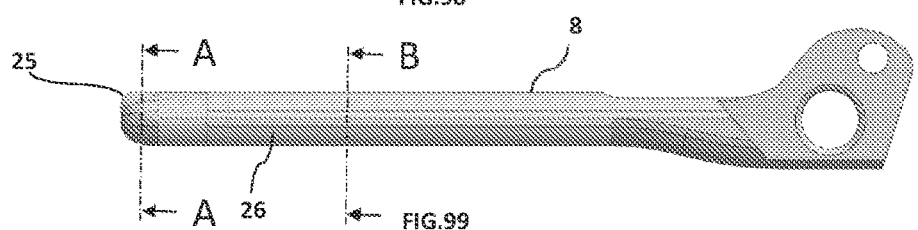
Figure 106:
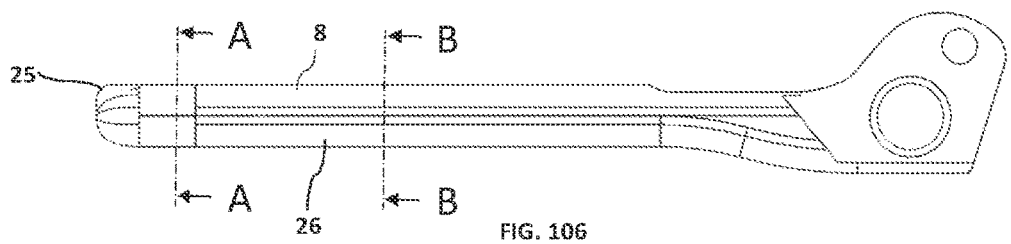

FIG. 99 and FIG. 106 illustrates the front view of the moving jaw 4 of the jaw assembly 1 along with section A-A and section B-B, showing pointed projection 25 at the substantially front edge or front part or front tip 29 of the jaw and also showing substantially half side insulation 26 leaving an area of the tip and substantially near the tip region non insulated 58.

Figure 100:
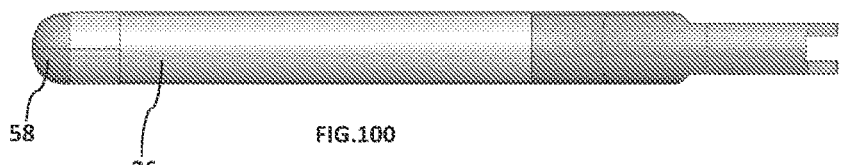
Figure 107:
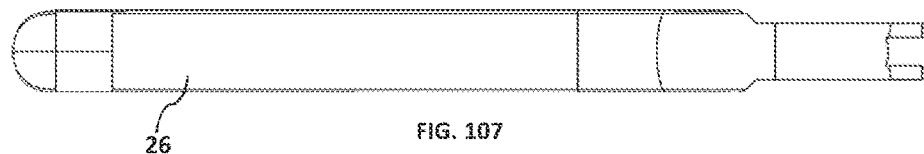

FIG. 100 and FIG. 107 illustrates the bottom view of the moving jaw 4 with substantial half side insulation 26 at back side leaving an area of the tip and substantially near the tip region non insulated 58.

Figure 101:
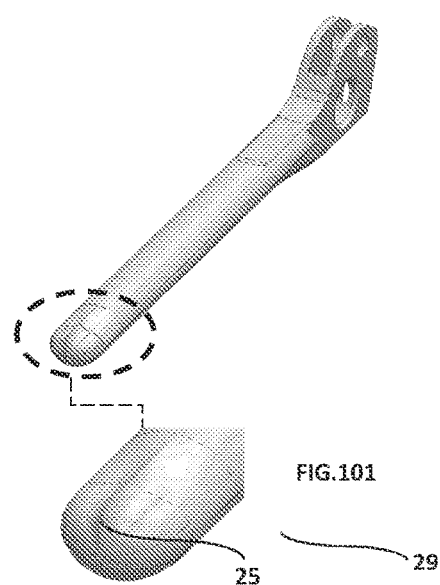
Figure 108:
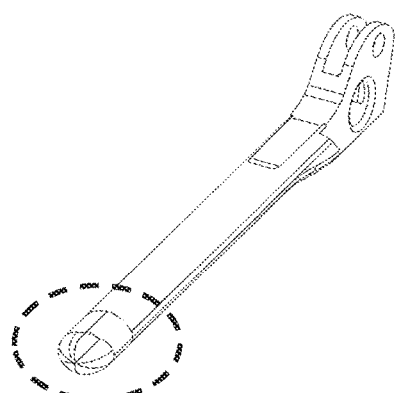

FIG. 101 and FIG. 108 illustrates the isometric view of the moving jaw 4 of the jaw assembly 1 showing "detailed view" of the pointed projection 25 at the substantially front edge or front part or front tip 29 of the jaw.

Figure 102:
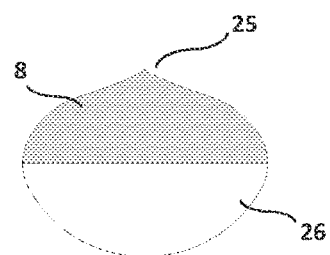
Figure 109:
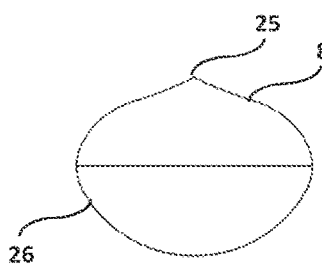

FIG. 102 and FIG. 109 along with FIG. 99 and FIG. 106 illustrates the sectional view A-A of the jaw showing substantially half side TiN coating 8 with pointed projection at the substantially front edge or front part or front tip 29 and substantial half side insulation 26.

Figure 103:
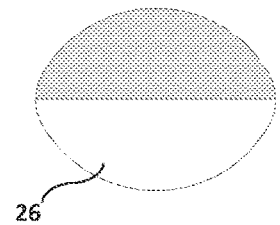
Figure 110:
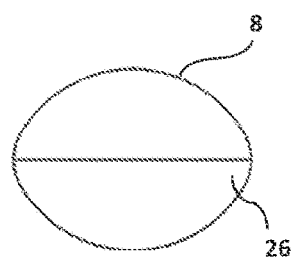

FIG. 103 and FIG. 110 along with FIG. 99 and FIG. 103 illustrates the sectional view B-B of the jaw other than the front edge or front part or front tip 29 with substantially half side insulation 26 and substantially half side conductive TiN coating 8.

Figure 104:
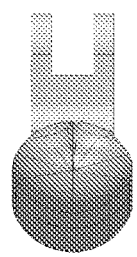

FIG. 104 and FIG. 111 illustrates the side view of the jaw assembly showing pointed projection 25 at the tip.

In an embodiment, the substantially front edge or front part or front tip 29 can be not having half side insulation 26.

In another embodiment, the jaws can be without substantially half side insulation 30. The projection can be pointed, blunt, sharp, or any other form as per requirement of the design.

FIG. 112 and FIG. 119 illustrates the top view of the fixed jaw 5 having elevated portion 27 at the substantially front edge or front part or front tip 29 of the jaw.

FIG. 113 and FIG. 120 illustrates the front view of the fixed jaw 5 of the jaw assembly 1, where it has elevated portion 27 at the substantially front edge or front part or front tip 29 of the jaw.

FIG. 114 and FIG. 121 illustrates the bottom view of the fixed jaw 5 with substantial half side insulation 26 leaving an area of the tip and substantially near the tip region non insulated 58. The pattern of partial DLC coating at the second portion 200 is more clearly illustrated in FIG. 111, 112, 113, where it illustrates the hollow open substantially central portion 55 for insertion of ceramic insert 45, and the pattern of DLC coating is sliding 52 in the front and straight 53 at the back with elevation 56 at further back portion on top side of jaw leaving a hollow substantially central portion for ceramic insert. The DLC coating is substantially straight 54 and has a small sliding 57 inwardly at the bottom side of jaw leaving hollow substantially central portion 55 for ceramic insert 45.

FIG. 115 and FIG. 122 illustrates the isometric view of the fixed jaw 5 of the jaw assembly 1 having elevated portion 27 at the substantially front edge or front part or front tip 29 of the jaw.

FIG. 116 and FIG. 123 along with FIG. 113 and FIG. 120 illustrates the sectional view A-A of the jaw showing TiN coating 8 with elevated portion 27 at the substantially front edge or front part or front tip 29. FIG. 117 and FIG. 124 along with FIG. 113 and FIG. 120 illustrates the sectional view B-B of the jaw other than the front edge or front part or front tip 29 with substantially half side insulation 26 and substantially half side TiN coating 8.

FIG. 118 and FIG. 125 illustrates the side view of the jaw assembly showing elevated portion 27 at the tip.
In an embodiment, the substantially front edge or front part or front tip 29 can be having half side insulation 26.

In another embodiment, the jaws can be without substantially half side insulation 26.

Figure 131:
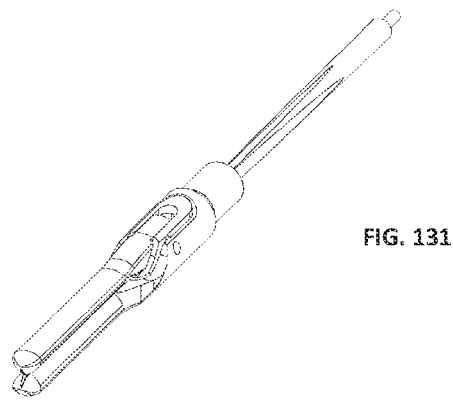

In another embodiment, FIG. 126 and FIG. 131 illustrates the isometric view of the jaw assembly (moving jaw and fixed jaw), working rod connection 6 and outer tube 16, where it shows the substantially half side insulation 30 at back side of at least one jaw of the jaw assembly 1 at the first portion 100 leaving an area of the tip and substantially near the tip region non insulated 58 and the substantial half side TiN coating 8 at the first portion and partial DLC coating 7 at the second portion 200 and optionally a ceramic insert 45 at the substantially central position within the partial DLC coating 7 or at peripheral position of the partial DLC coating 7. The jaws have concave shape (butterfly shape when joined together) 31 of jaw.

Figure 132:
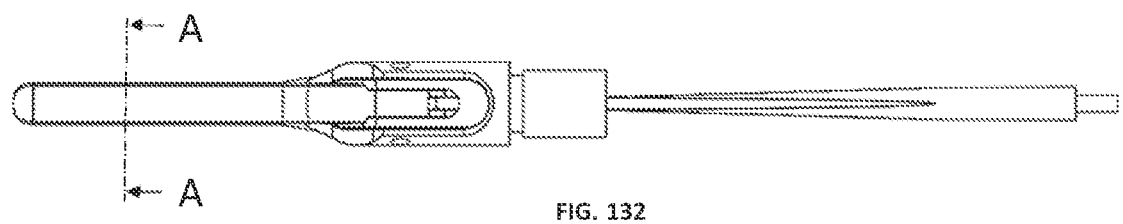
Figure 135:
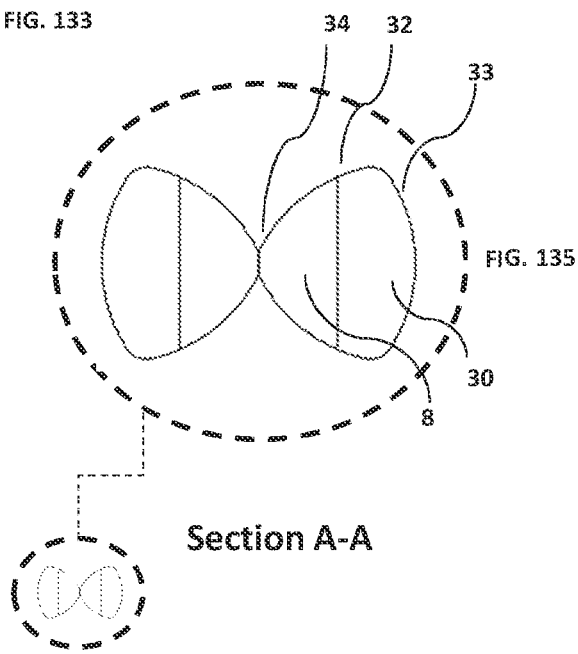

In another embodiment, FIG. 127 and FIG. 132 illustrates the top view of the jaw assembly illustrating moving jaw, rod and the outer tube, where it illustrates sectional view A-A in FIG. 130 and FIG. 135 which has concave shape (butterfly shape) 31 of jaw with substantially rounded sides 32 and round or flat top 33 to target the located and desired tissue to be cut at the narrowed substantially round base 34 to provide sealing and/or cutting. The back side is substantially half side insulated 30 to provide protection to the tissues in contact with the back portion of the jaw preventing unnecessary burning or cutting of tissue. The base may be narrow round, broad round.

In another embodiment, the jaws can be without substantially half side insulation 30.

Figure 133:

FIG. 128 and FIG. 133 illustrates the front view of the jaw assembly 1, working rod connection 6 and outer tube 16, and showing conductive first portion 100 having TiN coating 8 and partial DLC coating 7 substantially at the back portion which is the second portion 200.

The jaws can be single action jaw where one jaw is moving and one jaw is fixed, or it can be double action jaw where both the jaws are moving.

Figure 134:
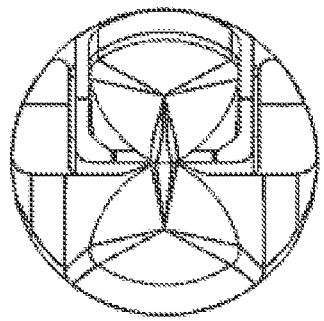

FIG. 129 and FIG. 134 illustrates the side view of the jaw assembly.

The jaw provides sealing and/or cutting structures such as peripheral coverings or folds before opening spaces.

Figure 141:
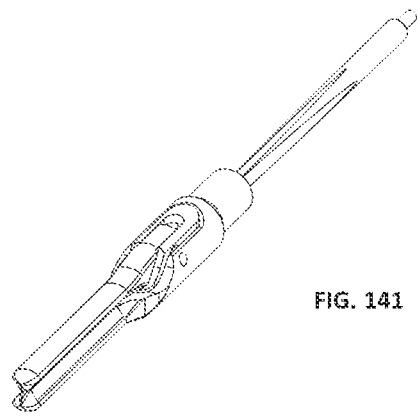

In another embodiment, FIG. 136 and FIG. 141 illustrates the isometric view of the jaw assembly 1 (illustrating moving jaw and fixed jaw), working rod connection 6 and outer tube 16, where it shows the substantially half side insulation 30 at back side of at least one jaw of the jaw assembly at the first portion 100 leaving an area of the tip and substantially near the tip region non insulated and the substantial half side TiN coating 8 at the first portion 100 and partial DLC coating 7 at the second portion 200 and optionally a ceramic insert at the substantially central position within the partial DLC coating 7 or at peripheral position of the partial DLC coating 7. The jaws have convex shape 35 of jaw.

Figure 142:
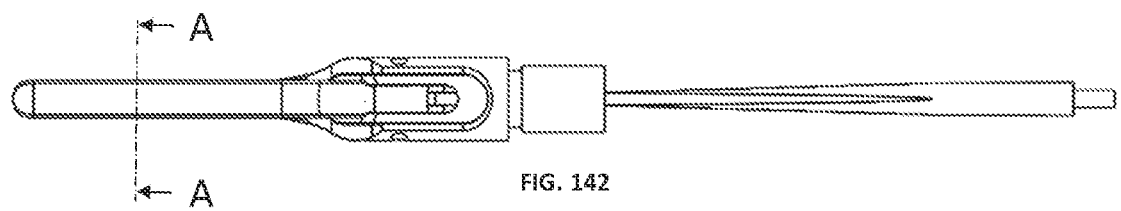
Figure 145:
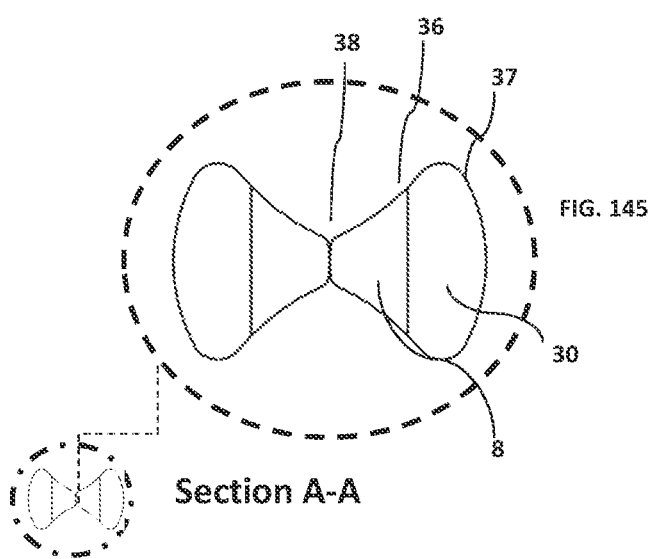

FIG. 137 and FIG. 142 illustrates the top view of the jaw assembly 1 (showing moving jaw), working rod connection 6 and the outer tube 16, where it illustrates sectional view A-A in FIG. 140 and FIG. 145 has convex shape 35 with substantially inward curve region 36 at the centre and rounded or flat top 37 of jaw to target the located and desired tissue to be cut at the narrowed substantially flat base 38 to provide sealing and/or cutting. The back region is substantially half side insulated 39 to provide protection to the tissues in contact with the back portion of the jaw preventing unnecessary burning or cutting of tissue. The top view also illustrates DLC coating 7 at the second portion 200 and optionally a ceramic insert at the substantially central position within the partial DLC coating 7 or at peripheral position of the partial DLC coating 7. The base can also be broad flat.

Figure 143:

FIG. 138 and FIG. 143 illustrates the front view of the jaw assembly, rod and outer tube, showing conductive first portion 100 having TiN coating 8 and partial DLC coating 7 substantially at the back portion which is second portion 200.

Figure 144:
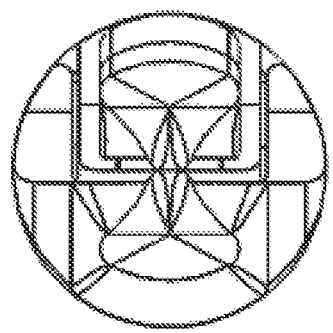

FIG. 139 and FIG. 144 illustrates the side view of the jaw assembly. The jaws can be single action jaw where one jaw is moving and one jaw is fixed, or it can be double action jaw where both the jaws are moving.

In another embodiment, the jaws can be without substantially half side insulation 30.

The jaws provide narrow but substantially flatter base due to this design for sealing and/or cutting vessel/tissue though the base may also be round in an embodiment. Its convex lateral shape offers more advantage to accommodate fatty thick pedicles.

Figure 151:
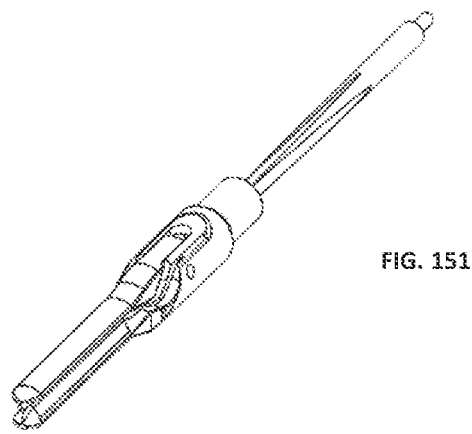

In another embodiment, FIG. 146 and FIG. 151 illustrates the isometric view of the jaw assembly 1, working rod connection 6 and outer tube 16, where it shows the substantially half side insulation 30 at the back side of at least one jaw of the jaw assembly at the first portion 100 leaving an area of the tip and substantially near the tip region non insulated and the substantial half side TiN coating 8 at the first portion 100 and partial DLC coating 7 at the second portion 200 and optionally a ceramic insert at the substantially central position within the partial DLC coating 7 or at peripheral position of the partial DLC coating 7.

Figure 152:
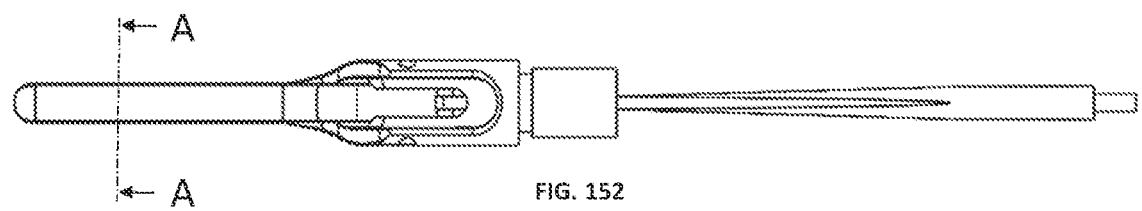
Figure 155:
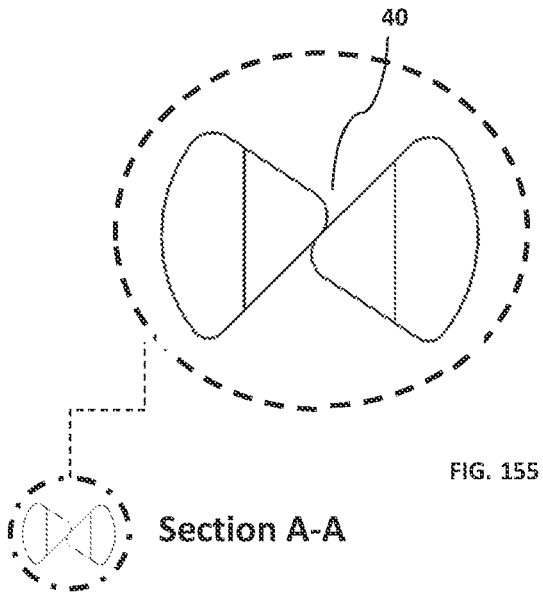

In another embodiment FIG. 147 and FIG. 152 illustrates the top view of the jaw assembly 1 (showing moving jaw), working rod connection 6 and the outer tube 16, where it illustrates sectional view A-A of the jaws in FIG. 150 and FIG. 155 which has concave or convex shape or triangular shape and where the jaws are crisscrossing 40 each other The back side is substantially half side insulated 30 to provide protection to the tissues in contact with the back portion of the jaw causing unnecessary burning or cutting of tissue. In an embodiment, any of the jaws described herein can also be criss cross if required or any shape like round jaw, elliptical jaw can be criss cross without limitation.

Figure 153:
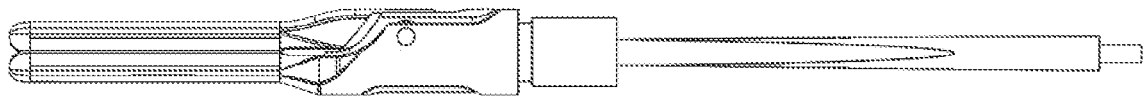

FIG. 148 and FIG. 153 illustrates the front view of the jaw assembly 1, working rod connection 6 and outer tube 16, showing conductive first portion 100 having TiN coating 8 and partial DLC coating 7 at the substantially back portion which is the second portion 200.

Figure 154:
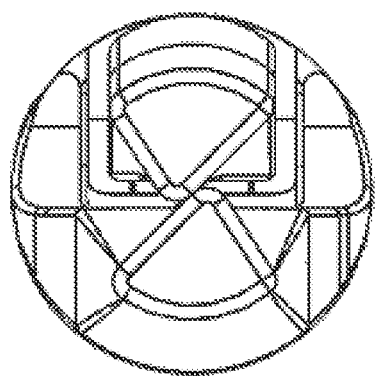

The jaws can be single action jaw where one jaw is moving and one jaw is fixed, or it can be double action jaw where both the jaws are moving. FIG. 149 and FIG. 154 illustrates the side view of the jaw assembly.

In another embodiment, the jaws can be without substantially half side insulation 30.

The jaws will provide a sharp scissor like effect at crisscrossing 40 regions to cut and/or seal the tissue. As opposed to previous designs used for cutting. This jaw design offers controlled cutting when tissue is less compressible and hard. It employs current at two different places to start cutting after sealing. It prevents short circuiting.

Figure 156:
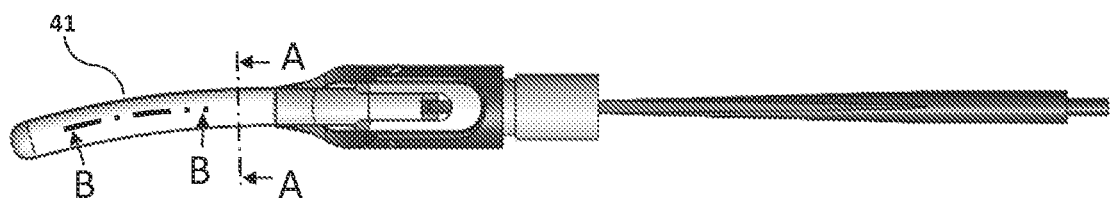
Figure 162:
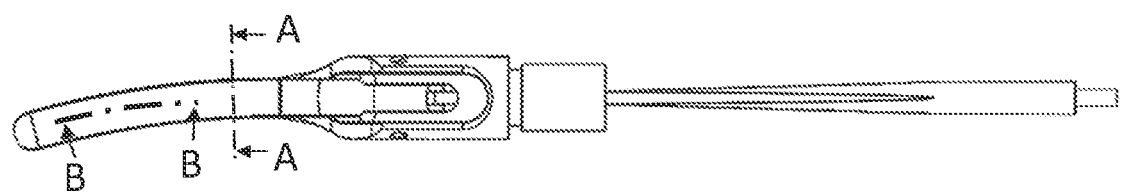

FIG. 156 and FIG. 162 illustrates the top view of the curved jaw 41 having substantially half side insulation 24 on back side of at least one jaw leaving an area of the tip and substantially near the tip region non insulated and partial DLC coating 7 and optionally a ceramic insert at the substantially central position within the partial DLC coating 7 or at peripheral position of the partial DLC coating 7.

Figure 157:
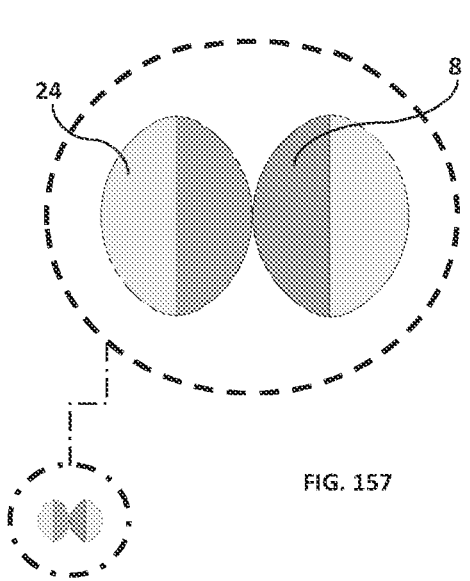
Figure 158:
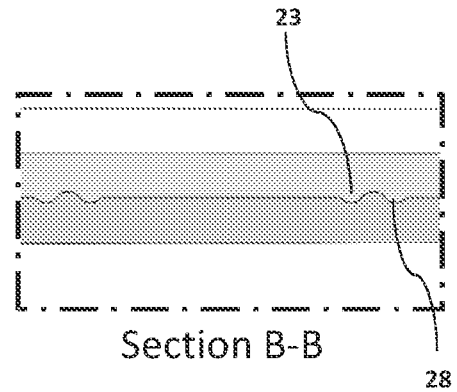

FIG. 156 illustrates the sectional View A-A in FIG. 157 and FIG. 163 that illustrates TiN coating portion 8 and substantially half side insulation 24 on back side, FIG. 156 illustrates sectional View B-B having projecting edges/ridges 23 on both jaws and groove 28 on both jaws into which the projecting edges/ridges enter shown in FIG. 158, FIG. 164.

Figure 159:
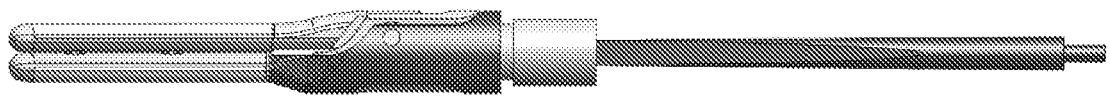
Figure 160:
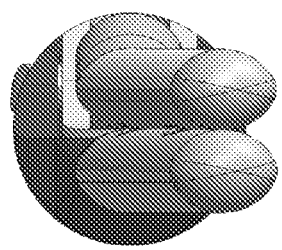
Figure 161:
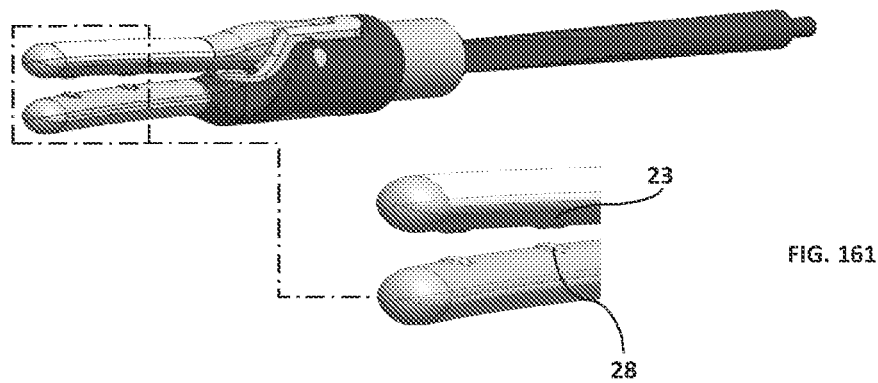
Figures 165, 166:
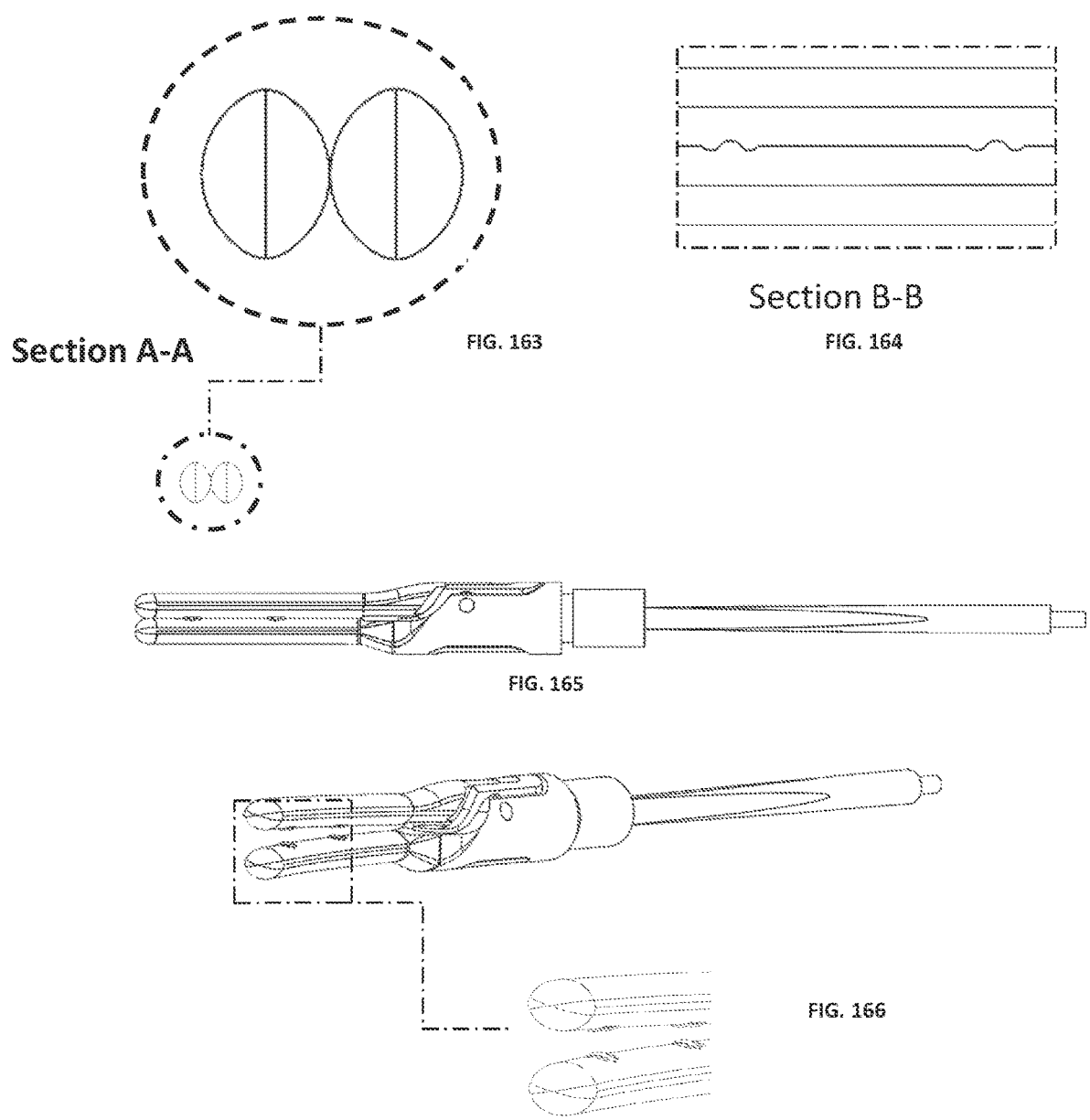

FIG. 159 and FIG. 165 illustrates the front view. FIG. 160 illustrates the side view of the jaw assembly with curved jaws 41. FIG. 161 and FIG. 166 illustrates the isometric view showing detail view of jaw.

In another embodiment, the jaws can be without substantially half side insulation 24 on back side.

Figure 167:
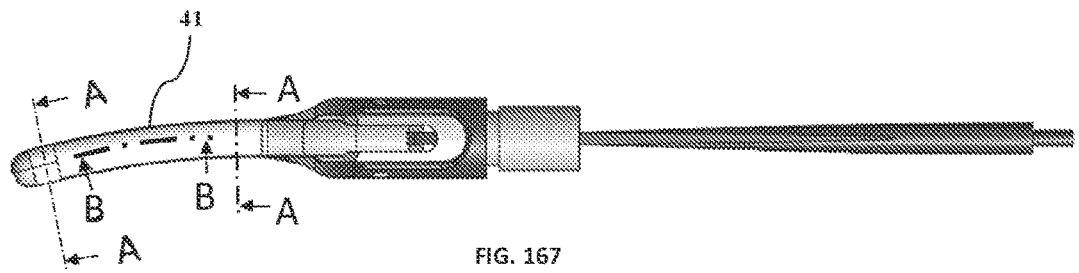

FIG. 167 and FIG. 173 illustrates the top view of the curved jaw 41 substantially half side insulation 26 on back side of at least one jaw 1 leaving an area of the tip and substantially near the tip region non insulated, and partial DLC coating land optionally a ceramic insert 45 at the substantially central position within the partial DLC coating 7 or at peripheral position of the partial DLC coating 7.

Figure 168:
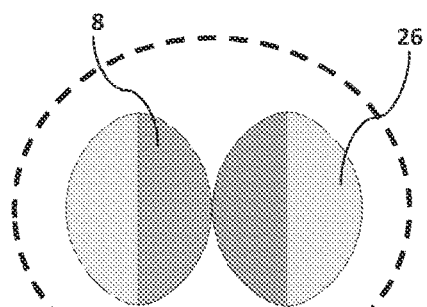

FIG. 168 and FIG. 174 illustrates the sectional View A-A from FIG. 167 and FIG. 173, which illustrates TiN coating portion 8 and substantially half side insulation 26

Figure 169:
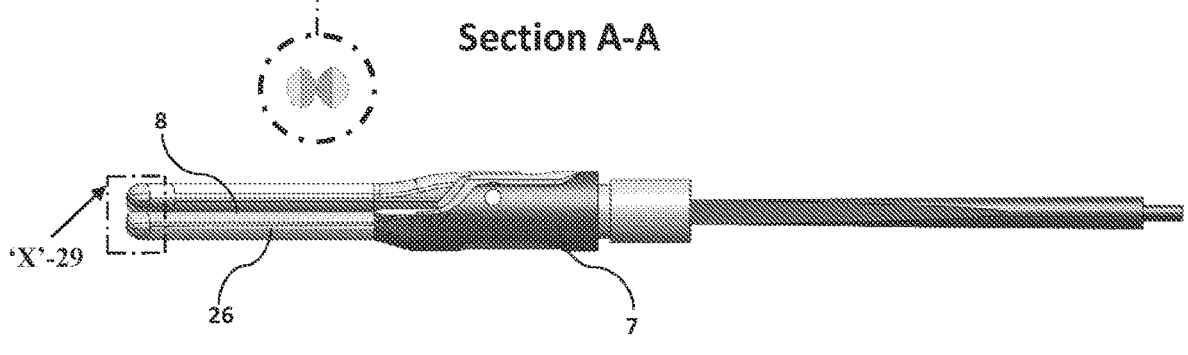
Figure 170:
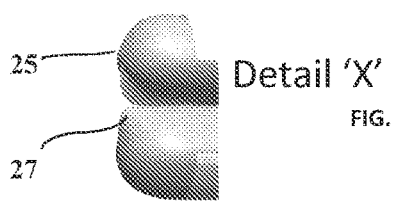
Figure 175:
Figure 176:
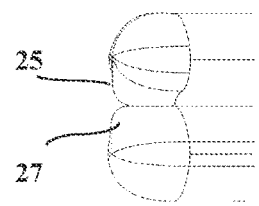

FIG. 169 and FIG. 175 illustrates the front view with "Detail View X" in FIG. 170 and FIG. 176 showing elevated portion 27 and pointed projection 25 at the TiN coating portion 8 front edge or front part or front tip 29.

Figure 177:
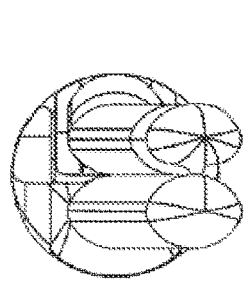
Figure 178:
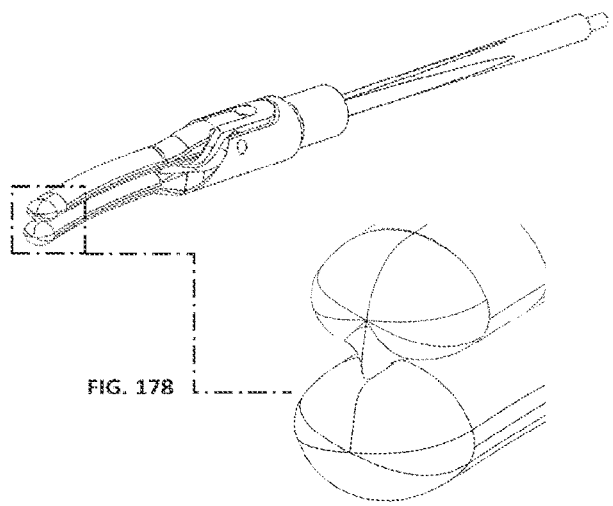

FIG. 171 and FIG. 177 illustrates the side view of the jaw assembly with curved jaws. FIG. 172 and FIG. 178 illustrates the isometric view showing detail view of jaw.

In another embodiment, the jaws can be without substantially half side insulation 26 on back side.

In another embodiment, FIG. 182 illustrates the bow like jaws when in cross sectional view. In FIG. 179 and FIG. 184 (Isometric views of moving jaw and fixed jaw) FIG. 183 and FIG. 188 (Side views), the construction of jaws are having substantially half side insulation 43 on back side till the tip and the sealer/cutter 45 with TiN coating 8 is embedded inside the insulated portion 43 in the centre where the cutter is thick and wide 44 when embedded in the insulated portion while it is tapered 42 as it moves down for cutting tissue.

In FIG. 180 and FIG. 185, is the top view where it illustrates substantially half side insulation 43 on back portion, also showing sectional view A-A in FIG. 182 and FIG. 187 having substantially half side insulation 43 and the sealer/cutter 45 with TiN coating 8 is embedded inside the insulated portion 43. FIG. 180 and FIG. 185 also illustrates partial DLC coating 7 and optionally a ceramic insert at the substantially central position within the partial DLC coating 7 or at peripheral position of the partial DLC coating 7.

In FIG. 181 and FIG. 186, is the front view where it has TiN coating 8 and DLC coating 7.

In another embodiment, the jaws can be without substantially half side insulation 43 on back portion.

Figure 189:
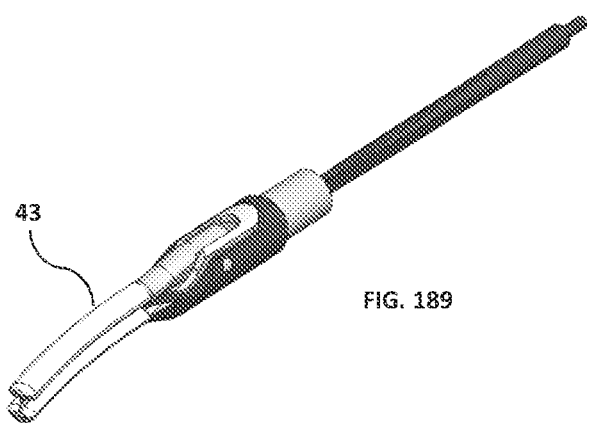
FIGS. 189-198 illustrates curved jaws with embedded sealer/cutter inside the jaws with substantially half side back insulation till the tip.
Figure 192:
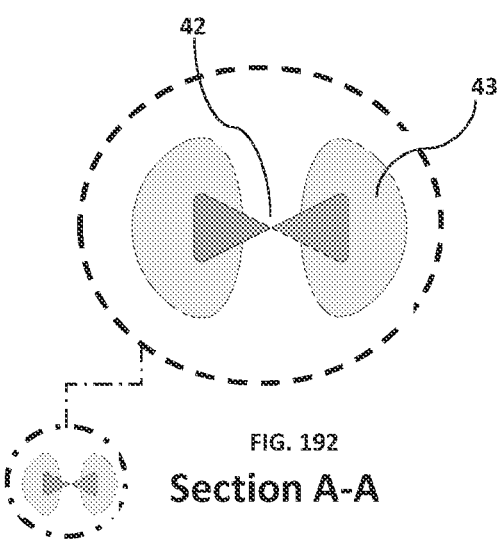
Figure 193:
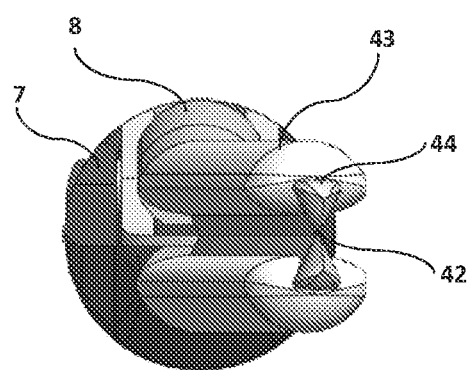
Figure 194:
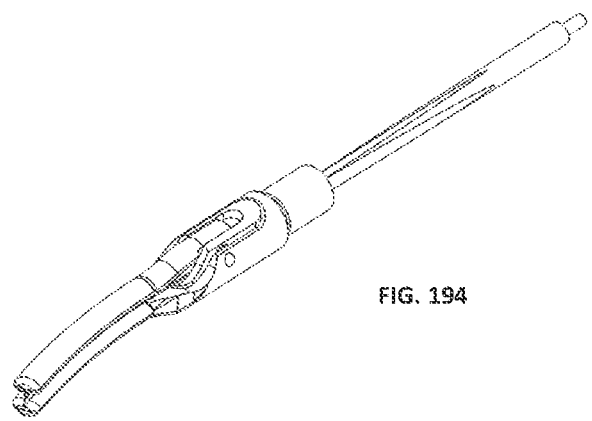
Figure 198:
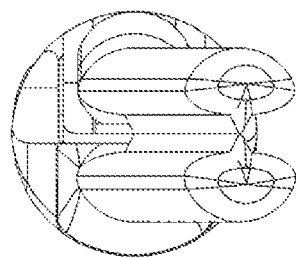

In another embodiment, FIG. 192 illustrates the bow like jaws when in cross sectional view. In FIG. 189 and FIG. 194 (Isometric views) FIG. 193 and FIG. 198 (Side views), the construction of curved jaw 41 having substantially half side insulation 43 on back portion and the sealer/cutter 45 with TiN coating 8 is embedded inside the insulated portion 43 substantially in the centre where the sealer/cutter is thick and wide 44 when embedded in the insulated portion while it is tapered 42 as it moves down for sealing and/or cutting tissue.

Figure 190:
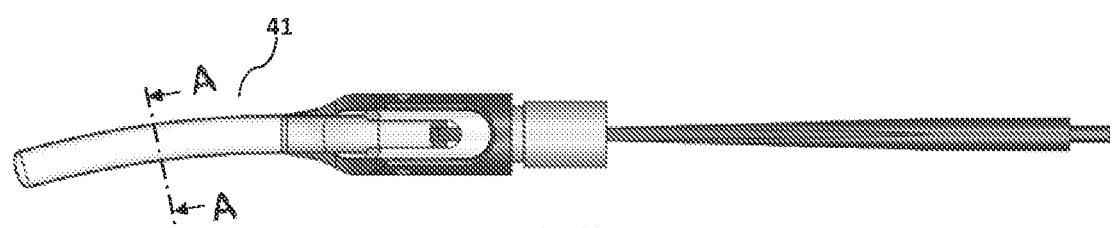
Figure 195:
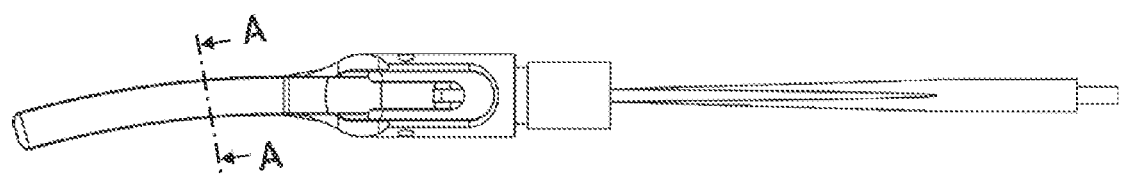
Figure 197:
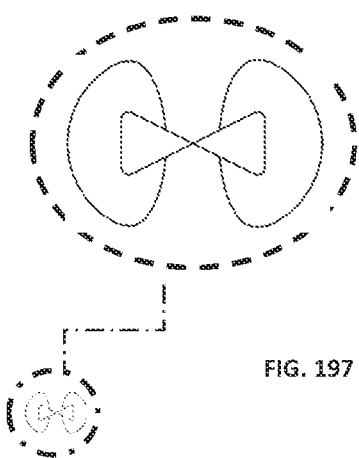

In FIG. 190 and FIG. 195, is the top view where the jaws are curved 41, it has substantially half side insulation 43 till the tip on back side, also showing sectional view A-A in FIG. 192 and FIG. 197 having substantially half side insulation 43 and the sealer/cutter 45 with. TiN coating Bis embedded inside the insulated portion 43. FIG. 190 and FIG. 195 also illustrates partial DLC coating 7 and optionally a ceramic insert at the substantially central position within the partial DLC coating 7 or at peripheral position of the partial DLC coating 7.

The insulation is till the tip that prevents the backside tissue from cutting because the sealer/cutter is open and sharp as differing from previous embodiments where the insulation is not till the tip on back side because the cutter is not open.

Figure 191:
Figure 196:

In FIG. 191 and FIG. 196, is the front view where it has TiN coating 8 and DLC coating 7.

In another embodiment, the jaws can be without substantially half side insulation 43 on back portion. The jaw can be fixed jaw, moving jaw or both the jaws can be moving.

The jaws can be single action jaw where one jaw is moving and one jaw is fixed, or it can be double action jaw where both the jaws are moving.

In an embodiment, the back side insulation may not be till the tip.

The jaw provides sealing and/or cutting structures such as peripheral coverings or folds before opening spaces.

It can be used in free spaces and thin multiple adhesions which avoid usage of cold scissors and saves time. The jaw can be used for direct sealing and/or cutting saving time and making the procedure easy as compared to previous methods of sealing first with one instrument and then cutting with another instrument.

In another embodiment, FIG. 199 and FIG. 205, illustrates the isometric view of the jaw assembly 1, wherein moving jaw is substantially elliptical jaw 49 and has a sharp protruding tip 46 resembling a beak on upper part of the jaw tip and flat region 51 on the rest of the part of the jaw tip, while the fixed jaw has a substantially round or U shaped jaw 48 having hollow space window 50 with insulation 47 on the tip at the area where the sharp protruding tip 46 of moving jaw touches the fixed jaw. The flat region 51 of elliptical jaw 49 is moved into the hollow space window 50 of the substantially round or U shaped jaw 48, the pointed beak like sharp protruding tip 46 presses on the insulation 47 at the tip of fixed jaw creating a sealing and cutting effect simultaneously. The tip can also be blunt as per requirement. The insulation on the tip can be with DLC coating, or ceramic or plastic.

FIG. 200 and FIG. 206, illustrates the top view and FIG. 201 and FIG. 207 illustrates the section B-B of the jaw assembly with partial DLC coating 7, working rod connection 6, outer tube 16 and TiN coating 8 with all the features explained above.

The insulation can be with DLC or any other preferable insulation material. The tip of moving jaw can be pointed, blunt, sharp, or any other form as per requirement of the design.

FIG. 200 and FIG. 206, illustrates the side view of the jaw assembly with partial DLC coating 7, working rod connection 6, outer tube 16 and TiN coating 8 with all the features explained above and displays the sectional C-C in FIG. 203 and FIG. 209.

FIG. 204 and FIG. 210, illustrates the sectional view of the jaw assembly.

In an embodiment, at least one jaw can have substantially half side back insulation at the back side leaving an area of the tip and substantially near the tip region non insulated.

Sealing and cutting is achieved together for thinner tissues, adhesions and small vessels thereby increasing the speed of the instrument. Short circuit and sparks are prevented from arising due to insulation at the tip of the jaw. Insulation prevents expansion of the jaw due to heat preventing the upper jaw from moving too much inside the window. The substantially round or U shaped jaw can be atraumatic for the tissue and also make the cleaning process of the jaw easier after surgery.

The back insulation in all the embodiments above is optional. In all the embodiments, wherever the jaws are sharp, it can optionally be blunt. The combination of the jaw shapes can be in variable combinations together or isolated without limitation either on moving jaw or fixed jaw of both moving jaw and fixed jaw, or on at least one jaw or both the jaws.

In all the embodiments above, cutting can also mean dissection, shearing, transecting. Sealing can also mean coagulating, or desiccation of tissue/vessel. The jaws prevent sticking and charring of tissue/vessel usually caused due to excess heat and temperature preventing extra burning of tissue/vessel and sparks, and preventing infection and accumulation of carbon in the body due to charring.

In all the embodiments above the half side back insulation can be extended till the tip or some distance short of tip.

In all the embodiments above, DLC can be coated partially without ceramic insert on the substantially back portion with ceramic insert or without ceramic insert.

In all the embodiments above only one jaw can have the shapes describes instead of both the jaws.

The present disclosure provides a jaw assembly with the instrument that can be made as reusable or disposable or partially disposable.

Figure 211:
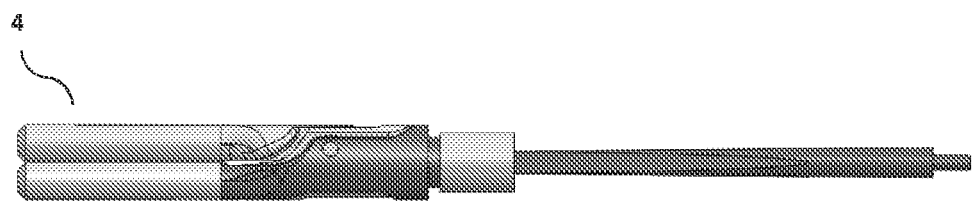
FIGS. 211-214 illustrates single action jaws.
Figure 212:
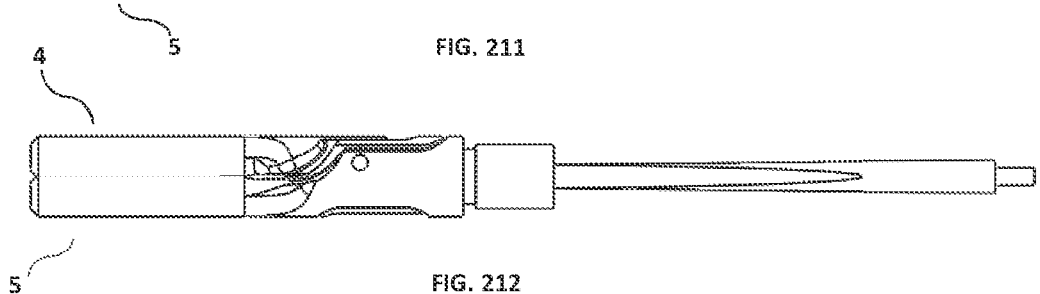

FIG. 211 and FIG. 212 illustrates the moving jaw and fixed jaw of the jaw assembly in closed state which can be application for all the embodiments above where one jaw is moving jaw 4 and another jaw is fixed jaw 5 or the jaws can be mentioned as single action jaw.

Figure 213:
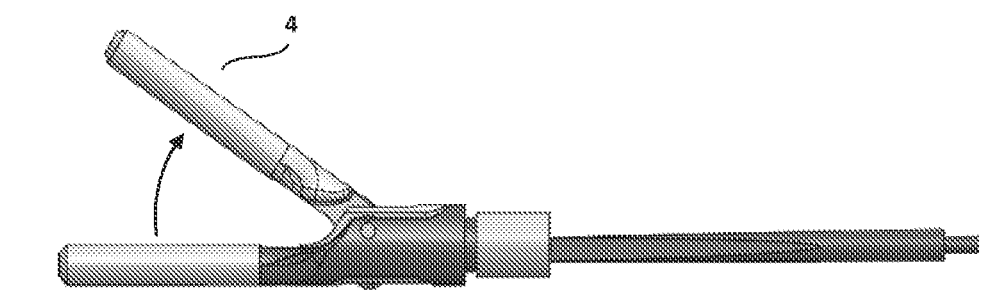
Figure 214:
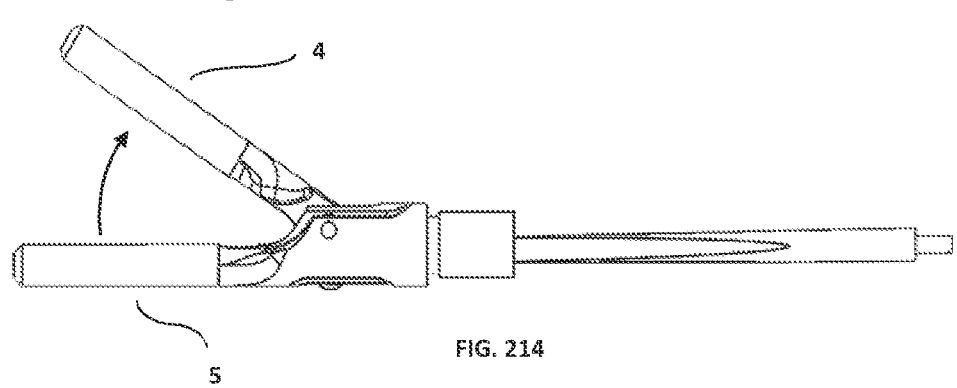

FIG. 213 and FIG. 214 illustrates the moving jaw and fixed jaw of the jaw assembly in open state which can be application for all the embodiments above where one jaw is moving jaw 4 and another jaw is fixed jaw 5 or the jaws can be mentioned as single action jaw.

Figure 215:
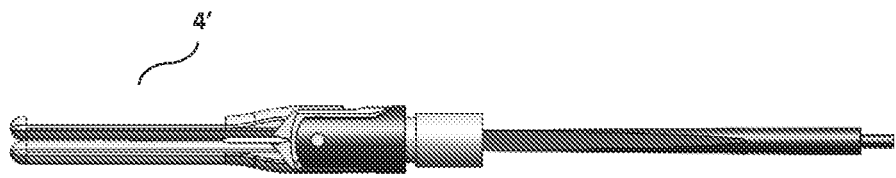
FIGS. 215-218 illustrates double action jaws.
Figure 216:
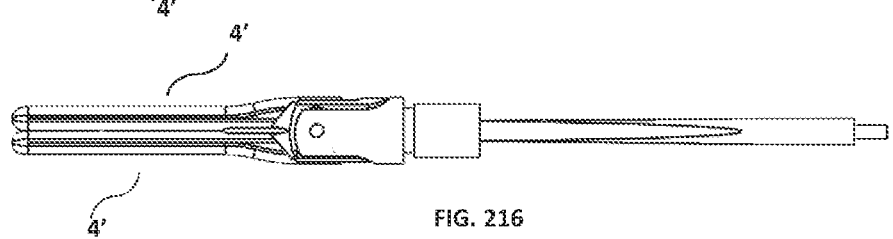

FIG. 215 and FIG. 216 illustrates the moving jaws of the jaw assembly in closed state which can be application for all the embodiments above where both the jaws are moving jaws 4' or the jaws can be mentioned as double action jaw.

Figure 217:
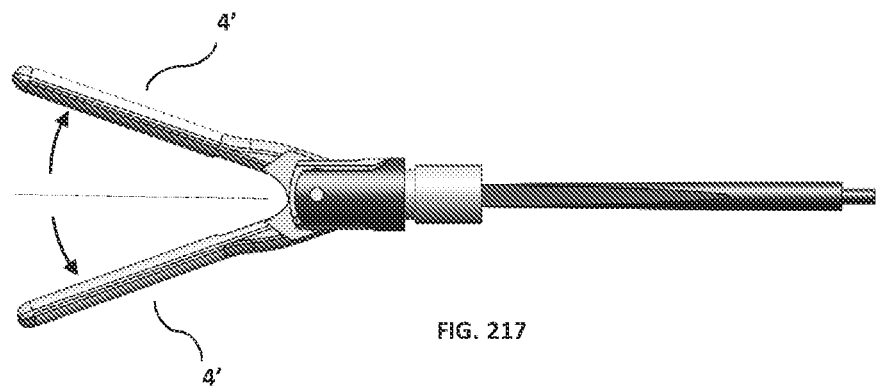
Figure 218:
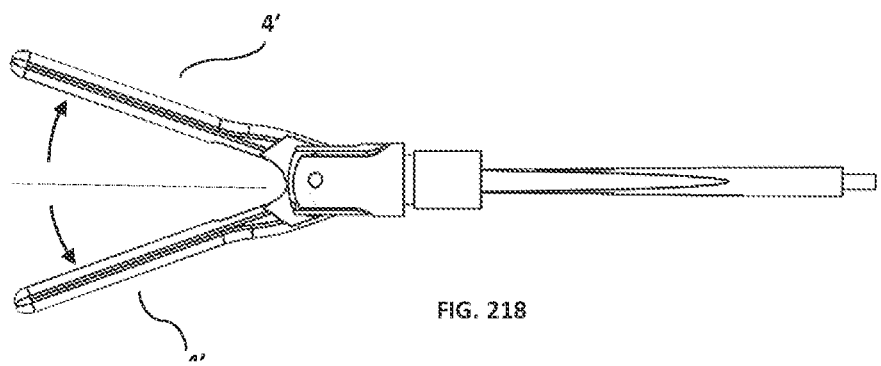

FIG. 217 and FIG. 218 illustrates the moving jaws of the jaw assembly in open state which can be application for all the embodiments above where both the jaws are moving jaws 4' or the jaws can be mentioned as double action jaw.

The use of any and all examples, or exemplary language (e.g. "such as") provided with respect to certain embodiments herein is intended merely to better illuminate the invention and does not pose a limitation on the scope of the invention otherwise claimed.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability.

We claim:

1. An advanced bipolar surgical instrument for sealing and cutting a tissue or vessel, comprising:
   a jaw assembly having two jaws (4,5) configured to act as electrodes, where the two jaws (4,5) include:
   a fixed jaw (5) having a first distal portion (100) and a second proximal portion (200), the first distal portion (100) being entirely distal of the second proximal portion (200), wherein:
   the first distal portion (100) is conductive, and includes a Titanium Nitride (TiN) coating (8) or a Titanium Nitride Silver (TiNAg) coating (8); and
   the second proximal portion (200) is non-conductive, includes a Diamond like Carbon (DLC) coating (7), and has therein an opening (55) where a ceramic insert (45) is inserted;
   a movable jaw (4) having a first distal portion (100) and a second proximal portion (200), the first distal portion (100) being entirely distal of the second proximal portion (200), the moving jaw (4) movable relative to the fixed jaw (5), wherein:

the first distal portion (100) is conductive, and includes a Titanium Nitride (TiN) coating (8) or a Titanium Nitride Silver (TiNAg) coating (8); and the second proximal portion (200) is conductive, or is non-conductive:

where conductive, the second proximal portion (200) includes a Titanium Nitride (TiN) coating (8) or a Titanium Nitride Silver (TiNAg) coating (8);

where non-conductive, the second proximal portion (200) includes a Diamond like Carbon (DLC) coating;

wherein the second portion (200) of the movable jaw (4) is movably connected within, and relative to, the ceramic insert (45) and the opening (55);

wherein the two conductive jaws (4, 5) are configured, when the tissue or vessel is grasped in between the first distal portions (100) of the two conductive jaws (4, 5), to achieve sealing and cutting by jaw heating due to a concentration of current at the first distal portion (100) of each of the two jaws (4, 5), where the tissue or vessel is held between a narrow base center portion of each of the first distal portions (100) of the two jaws (4, 5), the narrow base center portion defining where inside surfaces of the first, distal portions (100) meet, each narrow base center portion having a width less than an overall width of the respective first distal portion (100).

2. The advanced bipolar surgical instrument as claimed in claim 1, wherein the instrument is configured for use in a laparoscopic surgery, a minimally invasive surgery, a laparotomy surgery, an open surgery or a robotic surgery.

3. The advanced bipolar surgical instrument as claimed in claim 1, wherein the ceramic insert (45) and the Diamond like Carbon (DLC) coating (7) are bio friendly, can withstand high temperature, mechanical pressure, force, and shocks, have good dielectric strength and can also withstand repeated heating and cooling cycles.

4. An instrument as claimed in claim 1, wherein one or both of the first distal portions (100) of the movable and the fixed jaws (4, 5), further comprise a back insulation (14, 21, 24, 26, 30, 43), or a Delrin molding, or a ceramic molding, for prevention of unintentional tissue burn.

5. The advanced bipolar surgical instrument as claimed in claim 1, wherein the two conductive jaws (4, 5) are of an asymmetrical or symmetrical circular shape, triangular shape, elliptical shape, parrot beak shape, curved shape, straight shape, convex shape, concave shape, or bow-shape, or where a sharp-pointed projection is on one jaw and an elevated portion is on another jaw or where the two jaws are single action or double action.

6. The advanced bipolar surgical instrument as claimed in claim 1, wherein when the tissue or vessel is held between the distal portion of each jaw the proximal portion of the jaws are designed to make a gap that allows expansion of the tissue or vessel laterally, thereby reducing the thickness of the tissue or vessel compressed between the narrow base of each jaw, ensuring compression, and causing penetration of current to achieve sealing.

7. The advanced bipolar surgical instrument as claimed in claim 1, wherein:

the Diamond like Carbon (DLC) coating (7) which by virtue of semi-conductor properties and high resistance to electrosurgical current, provides an insulation property to the jaws by preventing sparks that arise due to a common meeting point of electric poles between an outer tube (16), from where a current passes to the movable jaw (4), and from a working rod connection (6), from where a current passes to the fixed jaw (5)

wherein either the Titanium Nitride (TiN) coating (8) prevents sticking and charring of the tissue or vessel due to current dispersion, or the Titanium Nitride Silver (TiNAg) coating (8) is configured to provide anti-microbial property to the jaws due to silver and to prevent growth of microbes around the tissue or vessel and on the jaws during a surgical procedure.

8. A method of advanced bipolar sealing and cutting of a tissue or vessel, the method comprising the steps of:

providing the advanced bipolar surgical instrument of claim 7, capable of tissue or vessel sealing; and achieving cutting of the tissue or vessel by jaw heating due to a concentration of current at the first distal portions of each jaw, where the tissue or vessel is held; and wherein the Titanium Nitride (TiN) coating (8) or the Titanium Nitride Silver (TiNAg) coating (8) of each first distal portion (100), and the Diamond like Carbon (DLC) coating (7) of the second proximal portion of the fixed lower jaw (5), enhance sealing and a cutting by increasing current concentration due to the collective properties of all coatings.

9. The method as claimed in claim 8, wherein the first distal portions (100) have a space there between, when the first distal portions (100) are in a non-engaged position with a tissue or vessel, the first distal portions (100) have an elliptical shape or a round shape in cross-section, and at least one first distal portion (100) is tapered at an upper, distal tip for targeting and picking of a tissue or vessel.

10. The method as claimed in claim 8, wherein the first distal portion of one jaw of the two jaws has a substantially elliptical shape in cross section, with a sharp or blunt protruding distal tip on an upper part of the distal tip, and the first distal portion of the other jaw of the two jaws has a substantially round or substantially U shape in cross-section, where the sharp or blunt protruding distal tip allows sharp simultaneous sealing and cutting of tissues or adhesions and prevents short circuit.

11. The method as claimed in claim 8, wherein when the tissue or vessel is held between the distal portion of each jaw the proximal portion of the jaws are designed to make a gap that allows expansion of the tissue or vessel laterally, thereby reducing the thickness of the tissue or vessel compressed between the narrow base of each jaw, ensuring compression, and causing penetration of current to achieve sealing.

* * * * *